United States Patent
Ku et al.

(10) Patent No.: US 12,291,567 B2
(45) Date of Patent: May 6, 2025

(54) ANTIBODIES TO GRANULOCYTE-MACROPHAGE COLONY STIMULATING FACTOR AND USES THEREOF

(71) Applicant: ELIXIRON IMMUNOTHERAPEUTICS (HONG KONG) LIMITED, Hong Kong (CN)

(72) Inventors: Cheng-Lun Ku, Taoyuan (TW); Yu-Fang Lo, Taoyuan (TW); Han-Po Shih, Taoyuan (TW); Jing-Ya Ding, Taoyuan (TW); Pei-Han Chung, Taipei (TW); Yin-Ping Wang, Taipei (TW)

(73) Assignee: Elixiron Immunotherapeutics (Hong Kong) Limited, Hong Kong (HK)

( * ) Notice: Subject to any disclaimer, the term of this patent is extended or adjusted under 35 U.S.C. 154(b) by 1030 days.

(21) Appl. No.: 17/198,229

(22) Filed: Mar. 10, 2021

(65) Prior Publication Data

US 2021/0309732 A1     Oct. 7, 2021

Related U.S. Application Data

(63) Continuation of application No. PCT/CN2019/110570, filed on Oct. 11, 2019.

(60) Provisional application No. 62/830,754, filed on Apr. 8, 2019, provisional application No. 62/745,602, filed on Oct. 15, 2018.

(51) Int. Cl.
    *C07K 16/24*     (2006.01)
    *G01N 33/68*     (2006.01)

(52) U.S. Cl.
    CPC ....... *C07K 16/243* (2013.01); *G01N 33/6863* (2013.01); *C07K 2317/21* (2013.01); *C07K 2317/24* (2013.01); *C07K 2317/33* (2013.01); *C07K 2317/565* (2013.01); *C07K 2317/567* (2013.01); *C07K 2317/92* (2013.01); *G01N 2333/535* (2013.01)

(58) Field of Classification Search
None
See application file for complete search history.

(56) References Cited

U.S. PATENT DOCUMENTS

| | | | |
|---|---|---|---|
| 7,867,495 B2 | 1/2011 | Steidl | |
| 8,017,748 B2 | 9/2011 | Raum | |
| 8,609,101 B2 | 12/2013 | Chan-Hui | |

FOREIGN PATENT DOCUMENTS

| | | |
|---|---|---|
| AU | 2013201228 | 3/2013 |
| CN | 107840885 | 3/2018 |
| CN | 107840886 | 3/2018 |
| EP | 3181585 | 6/2017 |
| JP | 5085533 B2 | 11/2012 |
| WO | 8704462 A1 | 7/1987 |
| WO | 9007936 A1 | 7/1990 |
| WO | 9011092 A1 | 10/1990 |
| WO | 9102805 A3 | 4/1991 |
| WO | 9114445 A1 | 10/1991 |
| WO | 9303769 A1 | 3/1993 |
| WO | 9310218 A1 | 5/1993 |
| WO | 9311230 A1 | 6/1993 |
| WO | 9319191 A1 | 9/1993 |
| WO | 9325234 A1 | 12/1993 |
| WO | 9325698 A1 | 12/1993 |
| WO | 9403622 A1 | 2/1994 |
| WO | 9423697 A1 | 10/1994 |
| WO | 9412649 A3 | 11/1994 |
| WO | 9428938 A1 | 12/1994 |
| WO | 9500655 A1 | 1/1995 |
| WO | 9513796 A1 | 5/1995 |
| WO | 9511984 A3 | 7/1995 |
| WO | 9507994 A3 | 8/1995 |
| WO | 9530763 A3 | 4/1996 |
| WO | 9617072 A3 | 4/1997 |
| WO | 9742338 A1 | 11/1997 |
| WO | 9958572 A1 | 11/1999 |
| WO | 0053211 A3 | 1/2001 |
| WO | 2013004806 A1 | 1/2013 |
| WO | 2017021631 A1 | 2/2017 |
| WO | 2018050111 A1 | 3/2018 |

OTHER PUBLICATIONS

Vajdos et al., Comprehensive Functional Maps of the Antigen-binding Site of an Anti-ErbB2 Antibody Obtained with Shotgun Scanning Mutagenesis. J. Mol. Biol. 320:415-428, 2002.*

Anonymous, "Study of Lenzilumab in Previously Treated Patients With Chronic Myelomonocytic Leukemia (CMML)—Full Text View—ClinicalTrials.gov", clinical trials.gov, (Sep. 10, 2015), pp. 1-7, URL: https://clinicaltrials.gov/ct2/show/NCT02546284?term=lenzilumab&cond=cancer&draw=2&rank=2, (Jan. 10, 2022), XP055877209.

Humanigen et al, "Humanigen Announces Preclinical Findings Presented on Lenzilumab's Potential to Optimize CAR-T Therapy", (May 2, 2018), URL: https://www.globenewswire.com/news-release/2018/05/02/1495378/0/en/Humanigen-Announces-Preclinical-Findings-Presented-on-Lenzilumab-s-Potential-to-Optimize-CAR-T-Therapy.html, (Jun. 26, 2020), XP055709355.

Internatioanl Search Report and Written Opinion issued in App. No. PCT/CN2019/110570, dated Jan. 15, 2020, 8 pages.

International Preliminary Report on Patentability issued in App. No. PCT/CN2019/110570, dated Apr. 29, 2021, 6 pages.

Scholz Tatjana et al, "GM-CSF in murine psoriasiform dermatitis: Redundant and pathogenic roles uncovered by antibody-induced neutralization and genetic deficiency", PloS one, United States, doi: 10.1371/journal.pone.0182646, (Jan. 1, 2017), pp. e0182646-e0182646, URL: https://journals.plos.org/plosone/article/file?id=10.1371/journal.pone.0182646&type=printable, (Mar. 24, 2022), XP055904894.

\* cited by examiner

*Primary Examiner* — Ruixiang Li
(74) *Attorney, Agent, or Firm* — FisherBroyles, LLP; Adam K. Whiting

(57) ABSTRACT

Disclosed herein are anti-GM-CSF antibodies capable of binding to human GM-CSF and blocking its biological activities. Also provided herein are pharmaceutical compositions comprising the anti-GM-CSF antibodies and therapeutic and diagnostic uses of such antibodies.

18 Claims, 13 Drawing Sheets

Specification includes a Sequence Listing.

FIG. 7C

ANTIBODIES TO GRANULOCYTE-MACROPHAGE COLONY STIMULATING FACTOR AND USES THEREOF

CROSS-REFERENCE TO RELATED APPLICATION

This application is a continuation of International Application No. PCT/CN2019/110570, filed Oct. 11, 2019, which claims priority benefit of U.S. Provisional Application No. 62/745,602, filed Oct. 15, 2018, and U.S. Provisional Application No. 62/830,754, filed Apr. 8, 2019, each of which is hereby incorporated by reference herein.

REFERENCE TO SEQUENCE LISTING

The official copy of the Sequence Listing is submitted with the specification as an ASCII formatted text file via EFS-Web, with a file name of "09793-004US1_SeqList.txt", a creation date of Jan. 2, 2025, and a size of 13,824 bytes. The Sequence Listing filed via EFS-Web is part of the specification and is incorporated in its entirety by reference herein.

BACKGROUND OF INVENTION

Granulocyte-macrophage Colony Stimulating Factor (GM-CSF), also known as colony-stimulating factor 2 (CSF2), is a monomeric glycoprotein secreted by macrophages, T cells, mast cells, natural killer cells, endothelial cells and fibroblasts that functions as a cytokine. GM-CSF stimulates hematopoietic stem cells to differentiate into myeloid lineage cells to produce granulocytes and monocytes.

In addition to its hematopoietic activity, GM-CSF induces differentiation, proliferation and activation of macrophages and dendritic cells which are necessary for the subsequent T helper cell type 1 and cytotoxic T lymphocyte activation. GM-CSF hematopoietic and non-hematopoietic functions have pro-inflammatory and immune regulatory potential.

GM-CSF signals via signal transducer and activator of transcription, STAT5 and stimulates the expression of STAT5 target genes. The GM-CSF/STAT5 signaling plays pivotal roles not only in maintaining immune homeostasis but also in exacerbating inflammatory responses.

It is therefore of great interest to develop new GM-CSF antagonists for use in treating diseases associated with the GM-CSF signaling.

SUMMARY OF INVENTION

The present disclosure, at least in part, is based on the development of anti-GM-CSF antibodies, e.g., 1D2 and its variants, which showed high binding affinity and specificity to human GM-CSF, and potent activities in inhibiting GM-CSF induced cell proliferation and cytokine production (e.g., IL8, and CCL17).

Accordingly, one aspect of the present disclosure relates to an isolated anti-GM-CSF antibody that bind to human GM-CSF (anti-GM-CSF antibodies). The anti-GM-CSF antibody disclosed herein may comprise a heavy chain variable domain ($V_H$), which comprises:
(i) a heavy chain complementary determining region 1 (HC CDR1) set forth as GYTFTX$_1$X$_2$Y, in which X$_1$ can be D, E, S, P, G, A, V, N, Q, C, W, R, T, or L; and X$_2$ can be K, V, L, E, P, S, T, C, D, R, H, A, F, Q, or N,
(ii) a heavy chain complementary determining region 2 (HC CDR2) set forth as INPX$_3$SGGT, in which X$_3$ can be K, L, M, E, H, S, V, N, C, F, P, W, G, A, I, R, T or Q, and
(iii) a heavy chain complementary determining region 3 (HC CDR3) set forth as ARGX$_4$DX$_5$X$_6$DX$_7$GAADL, in which X$_4$ can be R, V, S, A, C, L, P, I, T, G, M, E, or Q; X$_5$ can be Y, I, L, W, F, T, V, A, G, N, Y, or S; X$_6$ can be Y, N, P, S, K, R, G, W, D, Q, L, H, F, A, T, V, or M; and X$_7$ can be Q, S, T, M, N, G, V, L, E, or W.

The anti-GM-CSF antibody disclosed herein, may comprise a light chain variable domain ($V_L$), which comprises:
(i) a light chain complementary determining region 1 (LC CDR1) set forth as QGINSX$_8$, in which X$_s$ can be V, L, G, E, R, F, P, H, or Y,
(ii) a light chain complementary determining region 2 (LC CDR2) set forth as AAS, and
(iii) a light chain complementary determining region 3 (LC CDR3) set forth QQYYSX$_9$X$_{10}$RT, in which X$_9$ can be P, R, N or C, and X$_{10}$ can be V, C, D, L, E, P, or R.

In some embodiments, the isolated antibody comprises the same HC CDRs and LC CDRs as a reference anti-GM-CSF antibody, e.g. 1D2. In some examples, the isolated antibody disclosed herein, may comprises a $V_H$ comprising the amino acid sequence of SEQ ID NO: 1, 3 or 4 and/or a $V_L$ comprising the amino acid sequence of SEQ ID NO: 2.

Any of the antibodies disclosed herein may specifically bind human GM-CSF. Alternatively, the antibody may cross react with a non-human GM-CSF, for example, a GM-CSF of a non-human primate (e.g., Rhesus macaque).

Further, the instant disclosure provides an isolated antibody, which binds to the same epitope as antibody 1D2 or competes against antibody 1D2 from binding to human GM-CSF. In some examples, the isolated antibody disclosed herein, may comprise a HC CDR1, a HC CDR2, and a HC CDR3, which collectively contains no more than 10 amino acid variations, preferably no more than 8 amino acid variations, and more preferably no more than 5, 4, 3, 2 or 1 amino acid variations, as compared with the HC CDR1, HC CDR2, and HC CDR3 of antibody 1D2. The GM-CSF antibody disclosed herein may further comprises an LC CDR1, an LC CDR2, and an LC CDR3, which collectively contains no more than 10 amino acid variations, preferably no more than 8 amino acids variations, and more preferably no more than 5, 4, 3, 2 or 1 amino acid variations, as compared with the LC CDR1, LC CDR2 and LC CDR3 of antibody 1D2.

Alternatively or in addition, the isolated antibody disclosed herein, may comprise heavy chain variable domain ($V_H$) that is at least 85% identical to the heavy chain variable domain of antibody 1D2, and a light chain variable domain ($V_L$) that is at least 85% identical to the light chain variable domain of antibody 1D2.

Any of the isolated antibody disclosed herein may be a human antibody or a humanized antibody. In some examples, any of the anti-GM-CSF antibody described herein may be a full length antibody (e.g., an IgG molecule). Alternatively, the anti-GM-CSF antibody may be an antigen-binding fragment thereof.

Any of the anti-GM-CSF antibodies disclosed herein may be conjugated with a detectable label.

In another aspect, provided herein is a nucleic acid or a nucleic acid set, which collectively encode the antibody binding to any of the GM-CSF antibodies described herein. A nucleic acid set refers to two nucleic acid molecules one encoding the heavy chain and the other encoding the light chain of a multi-chain GM-CSF antibody disclosed herein. In some examples, the nucleic acid or nucleic acid set can be a vector or a vector set, for example, an expression vector or an expression vector set. Also provide herein are host cells comprising the vector or vector set disclosed herein. Such host cells can be bacterial cells, yeast cells, insect cells, plant cells, or mammalian cells.

In addition, the present disclosure features a pharmaceutical composition, comprising (a) a monoclonal antibody binding or antigen binding fragments to GM-CSF as disclosed herein, or the encoding nucleic acid(s), and (b) a pharmaceutically acceptable carrier. In some embodiments, the pharmaceutical acceptable carrier may comprise a buffering agent, a surfactant, a salt, an amino acid, an antioxidant, a sugar derivative (e.g., a non-reducing sugar, a sugar alcohol, a polyol, a disaccharide, or a polysaccharide). Such a pharmaceutical composition can be used for treating any of the target diseases also disclosed herein. Further, the present disclosure provides uses of the antibodies, the encoding nucleic acids, or other aspects relating to the antibody as disclosed herein for manufacturing a medicament for use in treatment of the target disease.

Further, the present disclosure features a method for modulating immune responses mediated by GM-CSF in a subject, the method comprising administering to a subject in need thereof an effective amount of the anti-GM-CSF antibody, or pharmaceutical composition comprising such. In some examples, the subject is a human patient having, suspected of having, or at risk for a disease, which is an inflammatory disease, an autoimmune disease or cancer.

Exemplary autoimmune diseases include, but are not limited to, rheumatoid arthritis, juvenile rheumatoid arthritis, spondyloarthropathy, ankylosing spondylitis, multiple sclerosis, psoriasis, plaque psoriasis, acute gouty arthritis, or osteoarthritis.

Exemplary inflammatory diseases include, but are not limited to, Kawasaki disease, chimeric antigen receptor T cell (CAR-T) induced cytokine release syndrome, CAR-T-induced related encephalopathy, diffuse parenchymal lung disease (DPLD), chronic obstructive pulmonary disease (COPD), aortic aneurysm, neuropathic pain, or graft-versus-host disease (GVHD).

Exemplary cancers include, but are not limited to, leukemia, gastric carcinoma, adenocarcinoma, mesothelioma, breast cancer, pancreatic ductal adenocarcinoma, colorectal cancer (CAC, for example, colitis-associated), or hypereosinophilic syndrome (HES). In some examples, the leukemia can be juvenile myelomonocyte leukemia (JMML), chronic myelomonocytic leukemia (CMML) or chronic eosinophilic leukemia.

In any of the methods disclosed herein, the subject has undergone or is undergoing an additional treatment of the disease.

Further, the present disclosure provides a method for producing an antibody binding to human GM-CSF, the method comprising: (i) culturing the host cell of expressing the anti-GM-CSF antibodies as disclosed herein under conditions allowing for expressing of the antibody that binds human GM-CSF; and (ii) harvesting the cultured host cell or culture medium for collection of the antibody that binds human GM-CSF. The method may further comprise (iii) purifying the antibody that binds human GM-CSF.

In addition, the present disclosure also provides a method for detecting presence of GM-CSF, the method comprising (i) contacting a biological sample suspected of containing GM-CSF with the antibodies disclosed herein, and (ii) measuring binding of the antibody to GM-CSF in the sample. The biological samples may be obtained from a human subject suspect of having or at risk of for a disease associated with GM-CSF. The contact step may be performed by administering the subject an effective amount of the anti-GM-CSF antibody.

The details of one or more embodiments of the invention are set forth in the description below. Other features or advantages of the present invention will be apparent from the following drawing and detailed description of several embodiments, and also from the appended claims.

BRIEF DESCRIPTION OF DRAWINGS

FIG. 1A is a chart showing the binding curve of 1D2 to GM-CSF. FIG. 1B is a chart showing the binding curve of antibody AMG203 (namilumab) to GM-CSF. FIG. 1C is a chart showing the binding curve of MOR103 (otilimab) to GM-CSF FIGS. 2A-2B include diagrams showing antibody 1D2 inhibits GM-CSF induced phosphorylation of STAT5 in human peripheral blood mononuclear cells (PBMCs) but not IL-3 induced STAT5 phosphorylation.

FIG. 5A is a chart showing the inhibition of GM-CSF induced TF-1 cell proliferation by 1D2-WT and SDR mutants (103N, 103N/32R and 103R/32R). FIG. 5B is a chart showing the inhibition of GM-CSF induced TF-1 cell proliferation by 1D2-WT and SDR mutants (32R, 54G, 94N, 100G, 103N, 103R, 105N, 54G/32R, 103N/32R, 103R/32R).

FIG. 6A is a schematic diagram showing the D89E (ED) mutant and D90E (DE) mutant antibodies of 1D2. FIGS. 6B-6D are binding curves of wild type antibody 1D2 (FIG. 6B), ED mutant antibody (FIG. 6C), DE mutant antibody (FIG. 6D) to GM-CSF by Surface plasmon resonance (SPR) using the Biacore 3000 instrument. FIG. 6E is a chart showing ED and DE mutant antibodies inhibit GM-CSF induced TF-1 cell proliferation at comparable level to wild type 1D2 antibody. FIG. 6F is a chart showing ED and DE mutant antibodies inhibit GM-CSF-induced IL-8 secretion by U937 cells at comparable level to wild type 1D2 antibody. FIG. 6G is a chart showing ED and DE mutant antibodies inhibit GM-CSF-induced CCL17 secretion by PBMCs at comparable level to wild type 1D2 antibody. FIG. 6H is a diagram showing the hydrophobicity profile of 1D2, ED and DE mutant antibodies by Hydrophobic interaction chromatography (HIC). FIG. 6I is a diagram showing the aggregation states of 1D2, ED and DE mutant antibodies by Dynamic light scattering (DLS) analysis.

FIGS. 7A-7C are charts showing cross-reactivity of anti-GM-CSF antibodies to GM-CSF antigen from different species. FIG. 7A is a chart showing the binding of AMG203, and 1D2 to human GM-CSF, mouse GM-CSF and rhesus GM-CSF. FIG. 7B is a chart showing the binding of 1D2, ED and DE mutants to human GM-CSF. FIG. 7C is a chart showing the binding of 1D2, ED and DE mutants to rhesus GM-CSF.

DETAILED DESCRIPTION OF INVENTION

Figure 1A:
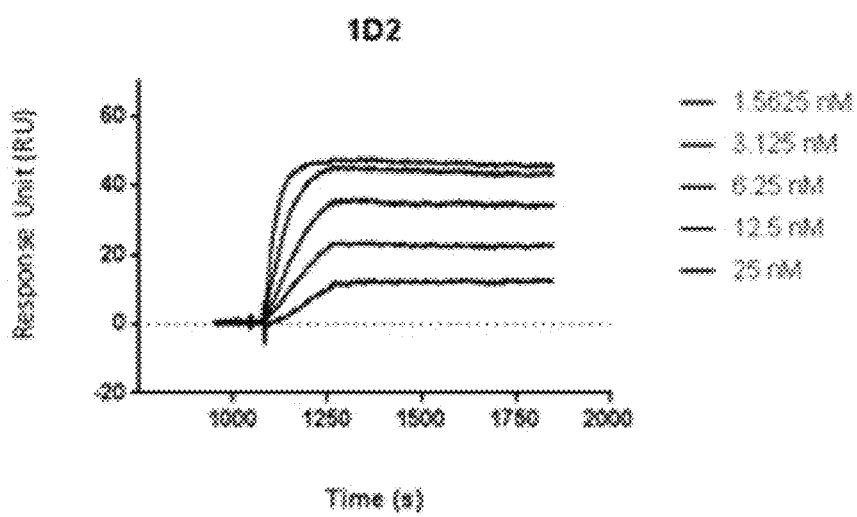
FIGS. 1A-1C are charts showing the binding curve of antibody 1D2 to human granulocyte-macrophage colony stimulating factor (GM-CSF) by Surface plasmon resonance (SPR) using the Biacore 3000 instrument (GE Healthcare).

The present disclosure, at least in part, is based on the development of anti-GM-CSF antibodies, e.g., 1D2 and its variants, which possessed unexpected superior features compared with known therapeutic anti-GM-CSF antibodies such as AMG203 and MOR103. For example, antibody 1D2 showed higher binding affinity (e.g., about 5- to 9-fold increase) to human GM-CSF relative to AMG203 and MOR103 as determined by surface plasmon resonance (SPR); potent blocking activity against the GM-CSF signaling (e.g., inhibiting STAT5 phosphorylation); potent inhibitory effect of GM-CSF induced cytokine production (e.g., IL-8 and CCL17) from immune cells (e.g., monocytes). Given the superior features of antibody 1D2, it would have been expected that this antibody and its functional variants would have advantageous features in blocking the GM-CSF signaling and thus benefiting treatment of diseases associated with GM-CSF as those described herein.

Accordingly, provided herein are antibodies capable of binding human GM-CSF, as well as nucleic acid encoding such antibodies, and uses thereof for both therapeutic and diagnostic purposes. Also provided herein are kits for therapeutic and/or diagnostic use of the antibodies, as well as methods for producing anti-GM-CSF antibodies.

I. Anti-GM-CSF Antibodies

The present disclosure provides isolated antibodies that bind to human granulocyte-macrophage colony stimulating factor (GM-CSF), for example, secreted GM-CSF.

An antibody (interchangeably used in plural form) is an immunoglobulin molecule capable of specific binding to a target antigen (e.g., GM-CSF in the present disclosure), through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information system® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). ee also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

In some embodiments, the isolated anti-GM-CSF antibody as described herein can bind and inhibit the activity of the GM-CSF by at least 50% (e.g., 60%, 70%, 80%, 90%, 95% or greater). The apparent inhibition constant (Kiapp or Ki,app), which provides a measure of inhibitor potency, is related to the concentration of inhibitor required to reduce enzyme activity and is not dependent on enzyme concentrations. The inhibitory activity of an anti-GM-CSF antibody described herein can be determined by routine methods known in the art.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-GM-CSF antibody described herein binds the same epitope in a GM-CSF antigen as a reference antibody disclosed herein (e.g., 1D2) or competes against the reference antibody from binding to the GM-CSF antigen. An "epitope" refers to the site on a target compound that is bound by an antibody such as a Fab or full length antibody. An epitope can be linear, which is typically 6-15 amino acid in length. Alternatively, the epitope can be conformational. An antibody that binds the same epitope as a reference antibody described herein may bind to exactly the same epitope or a substantially overlapping epitope (e.g. containing less than 3 non-overlapping amino acid residue, less than 2 non-overlapping amino acid residues, or only 1 non-overlapping amino acid residue) as the reference antibody. Whether two antibodies compete against each other from binding to the cognate antigen can be determined by a competition assay, which is well known in the art. Such antibodies can be identified as known to those skilled in the art, e.g., those having substantially similar structural features (e.g., complementary determining regions), and/or those identified by assays known in the art. For example, competition assays can be performed using one of the reference antibodies to determine whether a candidate antibody binds to the same epitope as the reference antibody or competes against its binding to the GM-CSF antigen.

In one example, the antibody used in the methods described herein can be a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

In some embodiments, the anti-GM-CSF antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (e.g., human GM-CSF) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (e.g., binding not detectable in a conventional assay).

In some embodiments, the antibodies described herein specifically binds to GM-CSF of a specific species (e.g., human GM-CSF) as relative to GM-CSF from other species. For example, the antibodies described herein may specifically binds to human GM-CSF as relative to mouse GM-CSF. In other embodiments, the antibodies described herein may cross-react with human GM-CSF and one or more GM-CSF from a non-human species (e.g., a non-human primate such as macaque). In some embodiments, the antibodies cross-react with human and rhesus macaque with similar binding affinity but have significantly lower binding affinity to mouse GM-CSF. In some embodiments, an anti-GM-CSF antibody as described herein has a suitable binding affinity for the target antigen (e.g., human GM-CSF) or antigenic epitopes thereof.

As used herein, "binding affinity" refers to the apparent association constant or KA, which is the ratio of association and dissociation constants, K-on and K-off, respectively. The KA is the reciprocal of the dissociation constant ($K_D$). The anti-GM-CSF antibody described herein may have a binding affinity ($K_D$) of at least $10^{-8}$, $10^{-9}$, $10^{-10}$ M, $10^{-11}$ M or lower for the target antigen or antigenic epitope. For example, the anti-GM-CSF antibody may have a binding affinity of $10^{-9}$ M, $10^{-10}$ M or lower to GM-CSF. An increased binding affinity corresponds to a decreased value of $K_D$. Higher affinity binding of an antibody for a first antigen relative to a second antigen can be indicated by a higher KA (or a smaller numerical value $K_D$) for binding the first antigen than the KA (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-GM-CSF antibodies described herein have a higher binding affinity (a higher KA or smaller $K_D$) to GM-CSF as compared to the binding affinity to another cytokines or chemokines (e.g., IL-6, IL1β, or TNFα). In some embodiments, the anti-GM-CSF antibody may have a higher binding affinity to a GM-CSF of a specific species (e.g., human GM-CSF) than that to a GM-CSF from a different species (e.g., mouse). Differences in binding affinity (e.g., for specificity or other comparisons) can be at least 1.5, 2, 2.5, 3, 4, 5, 10, 15, 20, 37.5, 50, 70, 80, 91, 100, 500, 1,000, 5,000, 10,000 or 105 fold. In some embodiments, any of the anti-GM-CSF antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance (SPR), florescent activated cell sorting (FACS) or spectroscopy (e.g., using a fluorescence assay). Exemplary conditions for evaluating binding affinity are in HBS-P buffer (10 mM HEPES pH7.4, 150 mM NaCl, 0.005% (v/v) surfactant P20) and PBS buffer (10 mM $PO_4$-3, 137 mM NaCl, and 2.7 mM KCl). These techniques can be used to measure the concentration of bound proteins as a function of target protein concentration. The concentration of bound protein ([Bound]) is generally related to the concentration of free target protein ([Free]) by the following equation:

[Bound]=[Free]/(Kd+[Free])

It is not always necessary to make an exact determination of KA, though, since sometimes it is sufficient to obtain a quantitative measurement of affinity, e.g., determined using a method such as ELISA or FACS analysis, is proportional to KA, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Provided below is an exemplary anti-GM-CSF antibody 1D2, including its heavy chain and light chain CDR sequences (by IMGT definition) and heavy chain and light chain variable domain sequences.

TABLE 1

Heavy chain and light chain CDR sequences of exemplary anti-GM-CSF antibody 1D2

| 1D2 | CDR1 | CDR2 | CDR3 |
|---|---|---|---|
| Heavy chain | GYTFTDKY (SEQ ID NO: 5) | INPKSGGT (SEQ ID NO: 6) | ARGRDYYDQGAADL (SEQ ID NO: 7) |
| Light chain | QGINSV (SEQ ID NO: 8) | AAS (SEQ ID NO: 9) | QQYYSPVRT (SEQ ID NO: 10) |

Heavy chain variable domain sequence of 1D2 (CDRs in boldface):

(SEQ ID NO: 1)
QVQLVQSGAEVKKPGASVKVSCEASGYTFTDKYLHWVRQAPGQGLEWMA

WINPKSGGTFYAQNFKGRVTVTRDTSINTAYLELTSLRLDDTSTYYCAR

GRDYYDQGAADLWGQGTMVTSS

Light chain variable domain of 1D2:

(SEQ ID NO: 2)
DIQLTQSPSSLSASVGDRVTITCRASQGINSVLAWYQQKPGKAPKLLLY

AASKLESGVPSRFSGSGSGTDYTLTISSLQPEDFGTYYCQQYYSPVRTF

GQGTKVEIKR

In some embodiments, an isolated anti-GM-CSF antibody disclosed herein may comprise the same regions/residues responsible for antigen-binding as a reference antibody (e.g., 1D2), such as the same specificity-determining residues (SDRs) in the CDRs or the whole CDRs. The regions/residues that are responsible for antigen-binding can be identified from amino acid sequences of the heavy chain/light chain sequences of the reference antibody by methods known in the art. See, e.g., www.bioinf.org.uk/abs; Almagro, J. Mol. Recognit. 17:132-143 (2004); Chothia et al., J. Mol. Biol. 227:799-817 (1987), as well as others known in the art or disclosed herein. In some embodiments, the anti-GM-CSF antibodies disclosed herein have the same $V_H$ and/or $V_L$ as a reference antibody, such as 1D2. In some embodiments, the anti-GM-CSF antibodies disclosed herein have the same heavy chain CDRs and/or light chain CDRs as a reference antibody, such as 1D2.

Furthermore, the antibody may comprise specificity-determining residues that are not found in the CDR sequences of a reference antibody (e.g., 1D2), but are included to develop antibodies with equivalent function to the reference antibody or to further refine and optimize antibody performance. Such antibodies, as used herein, are termed SDR mutant antibodies. In general, the antibody will comprise substantially all of at least one, and typically two, variable domains, in which all or substantially all of the CDR regions and all or substantially all of the FR regions consensus sequence. The antibodies may have one or more CDRs (one, two, three, four, five, six) which are altered with respect to the original antibody. Such residues can be identified by in vitro affinity maturation of a reference antibody (e.g., 1D2). Methods of performing in vitro affinity maturation of a reference antibody is known in the art, see e.g., Li et al, Mabs, 2014 March-April; 6(2):437-45.

In some embodiments, the SDR mutant antibodies have at least 20%, 30%, 40%, 50%, 60%, 70%, 80%, 85%, 90%, 95%, 96%, 97%, 98%, 99%, 100%, 105% or more binging affinity to GM-CSF as compared to the reference antibody, such as 1D2.

In some embodiments, the isolated anti-GM-CSF antibody comprises a heavy chain variable region that comprises a heavy chain CDR1 (HC CDR1), a heavy chain CDR2 (HC CDR2), and a heavy chain CDR3 (HC CDR3).

In some embodiments, following the IMGT definition, the HC CDR1 may comprise the amino acid sequence of $GYTFTX_1X_2Y$. $X_1$ can be D, E, S, P, G, A, V, N, Q, C, W, R, T, or L. For example, $X_1$ can be D, V, N, Q, C, W, or R. In one example, $X_1$ can be D. Alternatively or in addition, $X_2$ can be K, V, L, E, P, S, T, C, D, R, H, A, F, Q, or N. In some embodiments, $X_2$ can be K, V, E, P, S, T, C, D, R, H, Q, or N. In one example, $X_2$ can be K. Alternatively or in addition, the HC CDR2 may comprise the amino acid sequence of $INPX_3SGGT$, in which $X_3$ can be K, L, M, E, H, S, V, N, C, F, P, W, G, A, I, R, T or Q. In some examples, $X_3$ can be K, L, M, E, H, S, V, N, C, P, W, G, A, I, R, T, or Q. In one example, $X_3$ can be K. Alternatively or in addition, the HC CDR3 may comprise the amino acid sequence of $ARGX_4DX_5X_6DX_7GAADL$, in which $X_4$ can be R, V, S, A, C, L, P, I, T, G, M, E, or Q. In some examples, $X_4$ can be R, V, S, A, C, P, I, T, G, M, or E. In one example, $X_4$ can be R. Alternatively or in addition, $X_5$ can be Y, I, L, W, F, T, V, A, G, N, Y, or S. In some examples, $X_5$ can be Y, L, W, F, V, G, N, Y or S. In one example, $X_5$ can be Y. Alternatively or in addition, $X_6$ can be Y, N, P, S, K, R, G, W, D, Q, L, H, F, A, T, V, or M. In some examples, $X_6$ can be Y, N, P, S, K, R, G, W, D, Q, H, F, A, T, V, or M. In one example, $X_6$ can be Y. Alternatively or in addition, $X_7$ can be Q, S, T, M, N, G, V, L, E, or W. In some examples, $X_7$ can be Q, S, T, M, N, G, V, or E. In one example, $X_7$ can be Q.

The anti-GM-CSF antibody may comprise a light chain variable region that comprises a light chain CDR1 (LC CDR1), a light chain CDR2 (LC CDR2), and a light chain CDR3 (LC CDR3). In some embodiments, following the IMGT definition, the LC CDR1 may comprise the amino acid sequence of $QGINSX_8$, in which $X_s$ can be V, L, G, E, R, F, P, H, or Y. In one example, $X_s$ can be V. Alternatively or in addition, the LC CDR2 may comprise the amino acid sequence of AAS. Alternatively or in addition, the LC CDR3 may comprise the amino acid sequence of QQYYSX$_9$X$_{10}$RT, in which X$_9$ can be P, R, N or C. In some examples, X$_9$ can be P, R or C. In one example, X$_9$ can be P. Alternatively or in addition, X$_{10}$ can be V, C, D, L, E, P, or R. In one example, X$_{10}$ can be V.

Also, within the scope of the present disclosure are functional variants of any of the exemplary anti-GM-CSF antibodies as disclosed herein. A functional variant may contain one or more amino acid residue variations in the V$_H$ and/or V$_L$, or in one or more of the HC CDRs and/or one or more of the LC CDRs as relative to the reference antibody, while retaining substantially similar binding and biological activities (e.g., substantially similar binding affinity, binding specificity, inhibitory activity, anti-inflammatory activity, or a combination thereof) as the reference antibody.

Exemplary WT (e.g., 1D2 in second column) and SDR mutants comprising amino acids correspond to residues X$_1$-X$_{10}$ as described above are set forth in Table 2. The binding affinity of the SDR mutant antibody comprises each residue is listed under the residue. For example, an SDR mutant comprises a single mutation in HC CDR1 at the X$_1$ residue, which is E, has a binding affinity to GM-CSF of 63% as compared to the reference antibody (e.g., 1D2).

TABLE 2

Binding Affinity of 1D2 Variants as Compared with 1D2

| Residue | 1D2 WT | SDR mutants | | | | | | | |
|---|---|---|---|---|---|---|---|---|---|
| X$_1$ | D 100% | E 63% | S 47% | P 69% | G 58% | A 66% | V 71% | N 74% | Q 74% |
| X$_2$ | K 100% | V 90% | L 60% | E 94% | P 88% | S 78% | T 74% | C 86% | D 90% |
| X$_3$ | L 100% | M 106% | E 113% | H 74% | S 82% | V 74% | N 73% | C 76% | F 67% |
| X$_4$ | R 100% | V 74% | S 72% | A 76% | C 89% | L 69% | P 101% | I 80% | T 93% |
| X$_5$ | Y 100% | I 64% | L 86% | W 82% | F 71% | T 56% | V 71% | A 68% | G 89% |
| X$_6$ | Y 100% | N 130% | P 141% | S 85% | K 143% | R 115% | G 138% | W 139% | D 134% |
| X$_7$ | Q 100% | S 134% | T 133% | M 148% | N 156% | G 105% | V 155% | L 63% | E 173% |
|

CDR3, which collectively contains no more than 10 amino acid variations (e.g., no more than 9, 8, 7, 6, 5, 4, 3, 2 or 1 amino acid variation) as compared with the LC CDR1, LC CDR2, and LC CDR3 of the reference antibody. In some examples, an anti-GM-CSF antibody may comprise a LC CDR1, a LC CDR2, and a LC CDR3, at least one of which contains no more than 5 amino acid variations (e.g., no more than 4, 3, 2, or 1 amino acid variation) as the counterpart LC CDR of the reference antibody. In specific examples, the antibody comprises a LC CDR3, which contains no more than 5 amino acid variations (e.g., no more than 4, 3, 2, or 1 amino acid variation) as the LC CDR3 of the reference antibody.

In some embodiments, the isolated anti-GM-CSF antibody disclosed herein may comprise heavy chain CDRs that collectively are at least 80% (e.g., 85%, 90%, 95%, or 98%) identical to the heavy chain CDRs of a reference antibody such as 1D2. Alternatively or in addition, the antibody may comprise light chain CDRs that collectively are at least 80% (e.g., 85%, 90%, 95%, or 98%) identical to the light chain CDRs of the reference antibody. In some embodiments, the anti- GM-CSF antibody may comprise a heavy chain variable region that is at least 80% (e.g., 85%, 90%, 95%, or 98%) identical to the heavy chain variable region of a reference antibody such as 1D2 and/or a light chain variable region that is at least 80% (e.g., 85%, 90%, 95%, or 98%) identical to the light chain variable region of the reference antibody.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the anti-GM-CSF antibodies may include modifications to improve properties of the antibody, for example, stability, oxidation, isomerization and deamidation. In some instances, the antibody may comprise residues that are not found in the frame work (FR region) sequences of the reference antibody (e.g., 1D2).

In some embodiments, the FR region of the heavy chain variable region of the reference antibody (e.g., 1D2) comprises an Aspartic acid-Aspartic acid (DD) motif. A DD motif, as used herein, refers to two consecutive aspartic acid residues within the amino acid sequence of an antibody. During manufacturing, storage and in vivo, therapeutic antibodies are at risk for degradation via a number of pathways (e.g., chemical degradation). For example, isomerization of D residues and deamination of asparagine (N) residues are common pathways of antibody degradation. Non-limiting examples of D and N degradation sequence motifs are DD, NG, NN, NS, NT, DG, DS, DT, DH, In some embodiments, the antibodies described herein comprises a DD motif at position 89 and 90 of the heavy chain variable domain.

In some instances, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. In some instances, conservative substitutions of amino acids may include substitutions made amongst amino acids within the following groups: (a) E, D; (b) M, I, L, V; (c) F, Y, W; (d) K, R, H; (e) A, G; (f) S, T; and (g) Q, N.

In some embodiments, the antibodies described herein comprise mutations of the DD motif at position 89 and 90 of the heavy chain variable domain. In some embodiments, the antibodies described herein comprise a D89E (ED) or D90E (DE) mutation of the heavy chain variable domain.

Exemplary heavy chain variable domain sequences comprising the D89E (ED) or D90E (DE) mutations are:
Heavy chain variable domain sequences with D89E (ED) mutation (mutation in boldface):

(SEQ ID NO: 3)
QVQLVQSGAEVKKPGASVKVSCEASGYTFTDKYLHWVRQAPGQGLEWMA

WINPKSGGTFYAQNEKGRVTVTRDTSINTAYLELTSLRLEDTSTYYCAR

GRDYYDQGAADLWGQGTMVTVSS

Heavy chain variable domain sequences with D90E (ED) mutation:

(SEQ ID NO: 4)
QVQLVQSGAEVKKPGASVKVSCEASGYTFTDKYLHWVRQAPGQGLEWMA

WINPKSGGTFYAQNFKGRVTVTRDTSINTAYLELTSLRLDETSTYYCAR

GRDYYDQGAADLWGQGTMVTVSS

In some embodiments, the antibody described here in comprises a $V_H$ comprising the amino acid sequence of SEQ ID NO: 1, 3 or 4, and/or a $V_L$ comprising the amino acid sequence of SEQ ID NO: 2.

In some embodiments, the heavy chain of any of the anti-GM-CSF antibodies as described herein may further comprise a heavy chain constant region (5 CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. In one example, the heavy chain constant region is of subclass IgG1.

The light chain of any of the anti-GM-CSF antibodies described herein may further comprise a light chain constant region (CL), which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

In one particular example, the anti-GM-CSF antibody disclosed herein is an IgG1/kappa full-length antibody.

As described herein, the anti-GM-CSF antibody can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies.

II. Preparation of Anti-GM-CSF Antibodies

Antibodies capable of binding GM-CSF as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., GM-CSF) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of GM-CSF. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XenomouseR™ from Amgen, Inc. (Fremont, CA) and HuMAb-MouseR™ and TC Mouse™ from Medarex, Inc. (Princeton, NJ) or H2L2 mice from Harbour Antibodies BV (Holland). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Genetically engineered antibodies, such as humanized antibodies, chimeric antibodies, single-chain antibodies, and bi-specific antibodies, can be produced via, e.g., conventional recombinant technology. In one example, DNA encoding a monoclonal antibody specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, human HEK293 cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Alternatively, techniques described for the production of single chain antibodies (U.S. Pat. Nos. 4,946,778 and 4,704,692) can be adapted to produce a phage or yeast scFv library and scFv clones specific to GM-CSF can be identified from the library following routine procedures. Positive clones can be subjected to further screening to identify those that inhibit GM-CSF activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In one example, epitope mapping can be accomplished use H/D-Ex (hydrogen deuterium exchange) coupled with proteolysis and mass spectrometry. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the GM-CSF polypeptide have been replaced (swapped) with sequences from a closely related, but antigenically distinct protein (such as CD-28 protein). By assessing binding of the antibody to the mutant GM-CSF, the importance of the particular antigen fragment to antibody binding can be assessed. Alternatively, competition assays can be performed using other antibodies known to bind to the same antigen to determine whether an antibody binds to the same epitope as the other antibodies. Competition assays are well known to those of skill in the art.

In some examples, an anti-GM-CSF antibody is prepared by recombinant technology as exemplified below. Nucleic acids encoding the heavy and light chain of an anti-GM-CSF antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV promoter, and the herpes simplex tk virus promoter.

Regulatable promoters can also be used. Such regulatable promoters include those using the lac repressor from *E. coli* as a transcription modulator to regulate transcription from lac operator bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-555115 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad, among others.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551(1992)] combined the tetracycline repressor (tetR) with the transcription activator (VP 16) to create a tetR-mammalian cell transcription activator fusion protein, tTa (tetR-VP 16), with the tetO bearing minimal promoter derived from the human cytomegalovirus (hCMV) promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen 5 et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art. Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-GM-CSF antibody, as also described herein. The recombinant expression vector can be introduced into a suitable host cell (e.g., a dhfr-CHO cell) by a conventional method, e.g., calcium phosphate mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-GM-CSF antibody and the other encoding the light chain of the anti-GM-CSF antibody. Both of the two recombinant expression vectors can be introduced into a suitable host cell (e.g., dhfr-CHO cell) by a conventional method, e.g., calcium phosphate-mediated transfection.

Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-GM-CSF antibody as described herein, vectors (e.g., expression vectors) containing such; and host cells comprising the vectors are within the scope of the present disclosure.

III. Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The anti-GM-CSF antibody containing pharmaceutical composition disclosed herein may further comprise a suitable buffer agent. A buffer agent is a weak acid or base used to maintain the pH of a solution near a chosen value after the addition of another acid or base. In some examples, the buffer agent disclosed herein can be a buffer agent capable of maintaining physiological pH despite changes in carbon dioxide concentration (produced by cellular respiration). Exemplary buffer agents include, but are not limited to a HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

In some embodiments, the buffer agent in the pharmaceutical composition described herein may maintain a pH value of about 5-8. For example, the pH of the pharmaceutical composition can be about 7.1, 7.2, 7.3, 7.4, 7.5, 7.6, 7.7, 7.8, 7.9, or 8.0. In other examples, the pharmaceutical composition may have a pH value lower than 7, for example, about 7, 6.8, 6.5, 6.3, 6, 5.8, 5.5, 5.3, or 5.

The pharmaceutical composition described herein comprises one or more suitable salts. A salt is an ionic compound that can be formed by the neutralization reaction of an acid and a base. (Skoog, D. A; West, D. M.; Holler, J. F.; Crouch, S. R. (2004). "chapters 14-16". Fundamentals of Analytical Chemistry (8th ed.)). Salts are composed of related numbers of cations (positively charged ions) and anions (negative ions) so that the product is electrically neutral (without a net charge). An ion, as described herein, are atoms or molecules which have gained or lost one or more valence electrons giving the ion a net positive or negative charge. If the chemical species has more protons than electrons, it carries a net positive charge. If there are more electrons than protons, the species has a negative charge.

A cation (+), as described herein, is an ion with fewer electrons than protons, giving it a positive charge. (Douglas W. Haywick, (2007-2008). "Elemental Chemistry"). A cation with one positive charge can be called a monovalent cation; a cation with more than one positive charge can be called a polyvalent or multivalent cation. Non limiting examples of monovalent cations are hydrogen ($H^+$), sodium ($Na^+$), potassium ($K^+$), ammonium ($NH^{4+}$), Lithium ($Li^+$), cuprous ($Cu^+$), silver ($Ag^+$), etc. Non limiting examples of multivalent cations are magnesium ($Mg^{2+}$), calcium ($Ca^{2+}$), barium ($Ba^{2+}$), beryllium ($Be^{2+}$), cupric ($Cu^{2+}$), ferrous ($Fe^{2+}$), ferric ($Fe^{3+}$), lead(II) ($Pb^{2+}$), lead(IV) ($Pb^{4+}$), manganese(II) ($Mn^{2+}$), strontium ($Sr^{2+}$), tin(IV) ($Sn^4$), zinc ($Zn^{2+}$), etc.

An anion, as described herein, is an ion with more electrons than protons, giving it a net negative charge. Non limiting examples of anions are azide ($N^{3-}$), bromide ($Br^-$), chloride ($Cl^-$), fluoride ($F^-$), hydride ($H^-$), iodide ($I^-$), nitride ($N^-$), Oxide ($O^{2-}$), sulfide (S2−), carbonate ($CO_3^{2-}$), hydrogen carbonate ($HCO_{3-}$), hydrogen sulfate ($HSO_4^-$), hydroxide ($OH^-$), dihydrogen phosphate ($H_2PO_4^-$), sulfate ($SO_4^{2-}$), sulfite ($SiO_3^{2-}$), silicate ($SiO_3^{2-}$), etc.

Suitable salts for use in the pharmaceutical compositions described herein may contain a monovalent cation and a monovalent or multi-valent anion. Alternatively, the salts for use in the pharmaceutical compositions described herein may contain a monovalent or multi-valent cation and a monovalent anion. Exemplary salts include, but are not limited to, potassium chloride (KCl), sodium chloride (NaCl), calcium chloride ($CaCl_2$)), Magnesium chloride ($MgCl_2$), Magnesium Sulfate ($MgSO_4$), Sodium Bicarbonate ($NaHCO_3$), Ammonium sulfate (($NH4)_2SO_4$), calcium carbonate ($Ca_2CO_3$), or a combination thereof.

The pharmaceutical composition described herein comprises one or more suitable surface-active agents, such as a surfactant. Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Suitable surfactants include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

A pharmaceutical composition, comprising an anti-GM-CSF described herein, may comprise one or more amino acids. Exemplary amino acids include, but are not limited to, In glycine, histidine, or arginine.

The pharmaceutical composition may also comprise one or more antioxidants. An antioxidant, as used herein, is an agent that prevents or delays oxidative degradation of the active ingredients contained in the composition. The antioxidants used herein may be phenolic antioxidants (sometimes called true antioxidants), reducing agents, or chelating agents. Phenolic antioxidants are sterically hindered phenols that react with free radicals, blocking the chain reaction. Reducing agents are compounds that have lower redox potentials and, thus, are more readily oxidized than the drug they are intended to protect. Reducing agents scavenge oxygen from the medium and, thus, delay or prevent drug oxidation. Chelating agents are sometimes called antioxidant synergists. Metal ions, such as $Co^{2+}$, $Cu^{2+}$, $Fe^{3+}$, $Fe^{2+}$, and $Mn^{2+}$, shorten the induction period and increase the oxidation rate. Trace amounts of these metal ions are frequently introduced to drug products during manufacturing. Chelating agents do not possess antioxidant activity as such, but enhance the action of phenolic antioxidants by reacting with catalyzing metal ions to make them inactive.

The pharmaceutical composition described herein may also comprise a sugar derivative. A sugar derivative, as used herein, encompasses sugars and organic compounds derived from sugar. In some examples, the sugar derivative can be a non-reducing sugar, a sugar alcohol, a polyol, a disaccharide or a polysaccharide.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and mcresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vnyl-alcohol)), polylactides (U.S. Pat. No. 3,773,919), copolymers of L-glutamic acid and 7 ethyl-L20 glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

In other examples, the pharmaceutical composition described herein can be formulated in a sustained release format, which affects binding selectively to tissue or tumors by implementing certain protease biology technology, for example, by peptide masking of the antibody's antigen binding site to allow selective protease cleavability by one or multiple proteases in the tumor microenvironment, such as Probody™ or Conditionally Active Biologics™. An activation may be formulated to be reversible in a normal microenvironment.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an 10 oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0. The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

IV. Therapeutic Applications

Any of the antibodies, as well as the encoding nucleic acids or nucleic acid sets, vectors comprising such, or host cells comprising the vectors, described herein are useful for treating GM-CSF mediated disorders. GM-CSF mediated diseases, as used herein, refer to any medical condition associated with increased levels of GM-CSF or increased sensitivity to GM-CSF. Non-limiting examples of GM-CSF mediated diseases are inflammatory diseases, autoimmune diseases, cancer, infectious diseases or other disorders requiring modulation of the immune response associated with GM-CSF.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having inflammatory diseases, autoimmune diseases, cancer, infectious diseases or other disorders requiring modulation of the immune response. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

The methods and compositions described herein may be used to treat inflammatory diseases. Non-limiting examples of inflammatory diseases are Kawasaki disease, chimeric antigen receptor T cell (CAR-T) induced cytokine release syndrome, CAR-T-induced related encephalopathy, diffuse parenchymal lung disease (DPLD), chronic obstructive pulmonary disease (COPD), aortic aneurysm, neuropathic pain, Graft-versus-host disease (GVHD), glomerulonephritis, epididymitis, atherosclerosis, erythropoietin resistance, graft versus host disease, transplant rejection, biliary cirrhosis, and alcohol-induced liver injury including alcoholic cirrhosis.

As used herein, Kawasaki disease is an illness that involves the skin, mouth, and lymph nodes, and most often affects kids under age 5. The cause is unknown, but if the symptoms are recognized early, kids with Kawasaki disease can fully recover within a few days. Untreated, it can lead to serious complications that can affect the heart.

The methods and compositions described herein may be used to treat autoimmune diseases. Examples of autoimmune diseases are rheumatoid arthritis including juvenile rheumatoid arthritis, Kawasaki disease, spondyloarthropathies including ankylosing spondylitis, inflammatory bowel diseases including ulcerative colitis and Crohn's disease, multiple sclerosis, Addison's disease, diabetes (type I), Graves' disease, Guillain-Barre syndrome, Hashimoto's disease, hemolytic anemia, systemic lupus erythematosus (SLE), lupus nephritis, myasthenia gravis, pemphigus, psoriasis, plaque psoriasis, psoriatic arthritis, autoimmune hepatitis-induced hepatic injury, rheumatic fever, sarcoidosis, scleroderma, and Sjogren's syndrome.

As used herein, "rheumatoid arthritis" refers to a type of autoimmune disease, which is characterized by synovial joint inflammations throughout the body. An early symptom of the disease is joint pain, which progresses into joint deformation, or damages in body organs such as in blood vessels, heart, lungs, skin, and muscles.

The methods and compositions described herein may be used to treat cancer. Examples of autoimmune diseases are leukemia, gastric carcinoma, adenocarcinoma, mesothelioma, breast cancer, pancreatic ductal adenocarcinoma, colitis-associated colorectal cancer (CAC), or hypereosinophilic syndrome (HES). In some examples, the leukemia can be is juvenile myelomonocyte leukemia (JMML), chronic myelomonocytic leukemia (CMML) or chronic eosinophilic leukemia.

The methods and compositions described herein may be used to treat cancer. Examples of cancers that may be treated with the methods and compositions described herein include, but are not limited to: leukemia, multiple myeloma, gastric carcinoma, skin cancer, lung cancer, melanoma, renal cancer, liver cancer, myeloma, prostate cancer, breast cancer, colorectal cancer, gastric cancer, pancreatic cancer, thyroid cancer, hematological cancer, lymphoma, leukemia, skin cancer, ovarian cancer, bladder cancer, urothelial carcinoma, head and neck cancer, metastatic lesion(s) of the cancer, and all types of cancer which are diagnosed for high mutational burden. In a particular embodiment, the cancer has a high mutation burden. Subjects having or at risk for various cancers can be identified by routine medical procedures.

As used herein, "an effective amount" refers to the amount of each active agent required to confer therapeutic effect on the subject, either alone or in combination with one or more other active agents. In some embodiments, the therapeutic effect is reduced GM-CSF activity, increased numbers of activated effector T cells, and/or reduced numbers or activity of regulatory T cells.

Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation.

It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily, weekly, every two weeks, or every three weeks dosage might range from about any of 0.1 µg/kg to 3 µg/kg to 30 µg/kg to 100 µg/kg to 300 µg/kg to 0.6 mg/kg, 1 mg/kg, 3 mg/kg, to 10 mg/kg, to 30 mg/kg to 100 mg/kg or more, depending on the factors mentioned above. For repeated administrations over several days, weeks, months, or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 3 mg/kg every 3 weeks, followed by a maintenance dose of about 1 mg/kg of the antibody once in 6 weeks, or followed by a maintenance dose of about 1 mg/kg every 3 weeks. However, other dosage regimens may be useful, depending on the pattern of pharmacokinetic decay that the practitioner wishes to achieve. For example, dosing of 1 mg/kg once in every 3 weeks in combination treatment with at least one additional immune therapy agent is contemplated. In some embodiments, dosing ranging from about 3 µg/mg to about 3 mg/kg (such as about 3 µg/mg, about 10 µg/mg, about 30 µg/mg, about 100 µg/mg, about 300 µg/mg, about 1 mg/kg, and about 3 mg/kg) may be used. In some embodiments, dosing frequency is once every week, every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.1 to 5.0 mg/kg may be administered. In some examples, the dosage of the anti-GM-CSF antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically, the clinician will administer an antibody, until a dosage is reached that achieves the desired result. In some embodiments, the desired result is a reduction of the size of the tumor, increased progression free survival period and/or overall survival. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder. Alleviating a target disease/disorder includes delaying the development or progression of the disease, or reducing disease severity.

Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

In some embodiments, the antibodies described herein are administered to a subject in need of the treatment at an amount sufficient to inhibit the activity of the target antigen by at least 20% (e.g., 30%, 40%, 50%, 60%, 70%, 80%, 90% or greater) in vivo. In other embodiments, the antibody is administered in an amount effective in reducing the activity level of a target antigen by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered parenterally, topically, orally, by inhalation spray, rectally, nasally, buccally, vaginally or via an implanted reservoir. The term "parenteral" as used herein includes subcutaneous, intracutaneous, intravenous, intraperitoneal, intratumor, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline. Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods and Applications of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 g to about 100 g of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history. In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents. Treatment efficacy for a target disease/disorder can be assessed by methods well-known in the art.

The anti-GM-CSF antibody and treatment methods involving such as described in the present disclosure may be utilized in combination with other types of therapy for the target disease or disorder disclosed herein. The term "in combination" in this context means that the antibody composition and the therapeutic agent are given either simultaneously or sequentially. Examples include chemotherapy, immune therapy (e.g. therapies involving anti-inflammatory drugs, immunosuppressant, therapeutic antibodies, antibodies, CAR T cells, or cancer vaccines), surgery, radiation, gene therapy, and so forth, or anti-infection therapy. Such therapies can be administered simultaneously or sequentially (in any order) with the treatment according to the present disclosure.

For example, the combination therapy can include the anti-GM-CSF antibody and pharmaceutical composition described herein, co-formulated with and/or co-administered with, at least one additional therapeutic agent. In one embodiment, the additional agent is a cancer chemotherapeutic agent e.g. oxaliplatin, gemcitabine, docetaxel. In another embodiment, the additional agent can be disease modifying antirheumatic drugs (DMARDs) e.g. methotrexate, azathioprine, chloroquine, hydroxychloroquine, cyclosporin A, sulfasalazine, for RA treatment. Such combination therapies may advantageously utilize lower dosages of the administered therapeutic agents, thus preventing possible toxicities or complications associated with the various monotherapies. Moreover, the additional therapeutic agents disclosed herein may act on pathways in addition to or distinct from the GM-CSF/STAT 5 pathway, and thus are expected to enhance and/or synergize with the effects of the anti-GM-CSF antibodies.

When the antibody composition described here is co-used with a second therapeutic agent, a sub-therapeutic dosage of either the composition or of the second agent, or a sub-therapeutic dosage of both, can be used in the treatment of a subject having, or at risk of developing a disease or disorder associated with the cell signaling mediated by GM-CSF. A "sub-therapeutic dose" as used herein refers to a dosage, which is less than that dosage which would produce a therapeutic result in the subject if administered in the absence of the other agent or agents. Thus, the sub-therapeutic dose of an agent is one which would not produce the desired therapeutic result in the subject in the absence of the administration of the anti-GM-CSF antibody described herein. Therapeutic doses of many agents that are in clinical use are well known in the field of medicine, and additional therapeutic doses can be determined by those of skill without undue experimentation. Therapeutic dosages have been extensively described in references such as Remington's Pharmaceutical Sciences, 18th ed., 1990; as well as many other medical references relied upon by the medical profession as guidance for the treatment of diseases and disorders. Additional useful agents see also Physician's Desk Reference, 59.sup.th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

V. Diagnostic Applications

Any of the anti-GM-CSF antibodies disclosed herein can also be used for detecting presence of GM-CSF (e.g., secreted GM-CSF) in vitro or in vivo. Results obtained from such detection methods can be used for diagnostic purposes (e.g., diagnosing diseases associated with secreted GM-CSF) or for scientific research purposes (e.g., identifying new GM-CSF secreting cell types, studying bioactivity and/or regulation of secreted GM-CSF). For assay uses such as diagnostic uses, an anti-GM-CSF antibody as described herein may be conjugated with a detectable label (e.g., an imaging agent such as a contrast agent) for detecting presence of GM-CSF (e.g., secreted GM-CSF), either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker.

Conjugated or attached can include covalent or noncovalent bonding as well as other forms of association, such as entrapment, e.g., of one entity on or within the other, or of either or both entities on or within a third entity, such as a micelle.

In one example, an anti-GM-CSF antibody as described herein can be attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for detecting GM-CSF secreting cells in vitro, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99}$mTc Mebrofenin, and $^{99}$mTc Red Blood Cells, $^{123}$I Sodium iodide, $^{99}$mTc Exametazime, $^{99}$mTc Macroaggregate Albumin, $^{99}$mTc Medronate, $^{99}$mTc Mertiatide, $^{99}$mTc Oxidronate, $^{99}$mTc Pentetate, $^{99}$mTc Pertechnetate, $^{99}$mTc Sestamibi, $^{99}$mTc Sulfur Colloid, $^{99}$mTc Tetrofosmin, Thallium-201, or Xenon-133.

The reporting agent can also be a dye, e.g., a fluorophore, which is useful in detecting a disease mediated by GM-CSF secreting cells in tissue samples.

To perform a diagnostic assay in vitro, an anti-GM-CSF antibody can be brought in contact with a sample suspected of containing GM-CSF, e.g., GM-CSF secreting cells or soluble GM-CSF in disease microenvironment. The antibody and the sample may be incubated under suitable conditions for a suitable period to allow for binding of the antibody to the GM-CSF antigen. Such an interaction can then be detected via routine methods, e.g., ELISA, histological staining or FACS.

To perform a diagnostic assay in vivo, a suitable amount of anti-GM-CSF antibodies, conjugated with a label (e.g., an imaging agent or a contrast agent), can be administered to a subject in need of the examination. Presence of the labeled antibody can be detected based on the signal released from the label by routine methods.

To perform scientific research assays, an anti-GM-CSF antibody can be used to study bioactivity of GM-CSF, detect the presence of GM-CSF intracellularly, and or regulating the effect of secreted GM-CSF. For example, a suitable amount of anti-GM-CSF can be brought in contact with a sample (e.g. a new cell type that is not previously identified as GM-CSF producing cells) suspected of producing GM-CSF. The cells are permeabilized prior to contacting the anti-GM-CSF antibody. The antibody and the sample may be incubated under suitable conditions for a suitable period to allow for binding of the antibody to the GM-CSF antigen. Such an interaction can then be detected via routine methods, e.g., ELISA, histological staining or FACS.

VI. Kits for Therapeutic and Diagnostic Applications

The present disclosure also provides kits for the therapeutic or diagnostic applications as disclosed herein. Such kits can include one or more containers comprising an anti-GM-CSF antibody, e.g., any of those described herein.

In some embodiments, the kit can comprise instructions for use in accordance with any of the methods described herein. The included instructions can comprise a description of administration of the anti-GM-CSF antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-GM-CSF antibody generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder treatable by modulating immune responses, such as autoimmune diseases. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-GM-CSF antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting secreted GM-CSF in a sample. Such a kit may comprise any of the anti-GM-CSF antibodies described herein. In some instances, the anti-GM-CSF antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-GM-CSF antibody. The kit may further comprise instructions for using the anti-GM-CSF antibody for detecting secreted GM-CSF.

IV. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B.

Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identification and Preparation of the Recombinant Anti-GM-CSF Antibodies (i) Isolation of Human B Cells Secreting Anti-GM-CSF Auto Antibodies and Identification of Anti-GM-CSF Antibodies CD3$^-$/CD19$^+$ B cells were isolated from human subjects by Fluorescence-activated Cell Sorting (FACS). CD3$^-$/CD19$^+$ B cells were further sorted for IgG producing B cells, which were subsequently tested for Granulocyte-macrophage colony-stimulating factor (GM-CSF) binding activity. B cells exhibited GM-CSF binding activity were sorted individually and amplified ex vivo (B cell clones). mRNA was extracted from each B cell clones and cDNA encoding the heavy chain variable domain ($V_H$) and the light chain variable domain ($V_L$) were obtained from reverse transcription.

(ii) Construction of Vector Sets for Expression of Anti-GM-CSF Antibodies

DNA fragments encoding the $V_H$ and $V_L$ of 1D2 were respectively cloned into a human IgG1κ expression vector containing a signal peptide as well as the human IgG1 constant region by GeneArt® Seamless Cloning and Assembly Enzyme Mix (Invitrogen). Competent E. coli (Biotech) were transformed with 5 μL of each recombinant vector, respectively. Colonies of the transformed E. coli were screened by PCR. PCR products of the expected size (about 1,800 bps) were sequenced for confirmation. Plasmid DNA was isolated using QIAprep® Spin columns (Qiagen) from 3 mL bacterial cultures of the transformed E. coli grown for 18 hours at 37° C. in Luria-Bertani broth containing 100 μg/mL ampicillin. In order to compare 1D2 with other anti-GM-CSF antibodies, DNA fragments encoding $V_H$ and $V_L$ from AMG203, and MOR103, which are anti-GMCSF antibodies currently being tested in Phase 2 clinical trials, were cloned into the human IgG1κ expression vector using the method described above.

The amino acid sequences of the variable heavy ($V_H$) chain and variable light ($V_L$) chain of the antibody of the present disclosure are listed in Table 3. The complementarity-determining regions (CDRs) were identified based on Kabat (Wu, T. T. and Kabat, E. A., 1970 J. Exp. Med. 132: 211-250) or IMGT systems (Lefranc M.-P. et al., 1999 Nucleic Acids Research, 27, 209-212). In Table 1, CDRs following "K:" were identified according to Kabat system, and CDRs following "I:" were identified according to IMGT system. The antibody of the present disclosure is named 1D2.

TABLE 3

Variable region and the complementarity-determining regions of 1D2.
(I: IMGT system; K: Kabat system)

variable heavy ($V_H$) chain

QVQLVQSGAEVKKPGASVKVSCEASGYTFTDKYLHWVRQAPGQGLE
WMAWINPKSGGTFYAQNFKGRVTVTRDTSINTAYLELTSLRLDDT
STYYCARGRDYYDQGAADLWGQGTMVTVSS (SEQ ID NO: 1)

| $V_H$ CDR1 | $V_H$ CDR2 | $V_H$ CDR3 |
|---|---|---|
| I: GYTFTDKY (SEQ ID NO: 5) | I: INPKSGGT (SEQ ID NO: 6) | I: ARGRDYYDQGAADL (SEQ ID NO: 7) |
| K: DKYLH (SEQ ID NO: 16) | K: WINPKSGGTFYAQNFKG (SEQ ID NO: 17) | K: GRDYYDQGAADL (SEQ ID NO: 18) | variable light ($V_L$) chain

DIQLTQSPSSLSASVGDRVTITCRASQGINSVLAWYQQKPGKAPKL
LLYAASKLESGVPSRFSGSGSGTDYTLTISSLQPEDFGTYYCQQYY
SPVRTFGQGTKVEIKR (SEQ ID NO: 2)

| $V_L$ CDR1 | $V_L$ CDR2 | $V_L$ CDR3 |
|---|---|---|
| I: QGINSV (SEQ ID NO: 8) | I: AAS (SEQ ID NO: 9) | I: QQYYSPVRT (SEQ ID NO: 10) |
| K: RASQGINSVLA (SEQ ID NO: 19) | K: AASKLES (SEQ ID NO: 20) | K: QQYYSPVRT (SEQ ID NO: 10) |

AMG203 (namilumab) and MOR103 (otilimab) are the therapeutic antibodies binding to human GM-CSF as known in the art. See, e.g., U.S. Pat. Nos. 8,017,748, 7,867,495.

(iii) Recombinant Antibody Production and Purification

ExpiCHO-S™ cells (Thermo Scientific, A29133) were seeded in a 125-mL flask in 30 mL of ExpiCHO-S™ expression medium (Thermo Scientific, A29100-01) and cultured under standard conditions. During exponential growing phage, 6×10$^6$ ExpiCHO-S™ cells were respectively transiently transfected with 20 μg of the vectors encoding 1D2, AMG203 or MOR 103 by ExpiFectamine™ CHO Transfection Kit (Thermo Scientific, A29129). 18-22 hours after transfection, ExpiFectamine™ CHO Enhancer and ExpiCHO™ Feed were added to the flask. The cells were cultured for 8 days. The supernatant of each culture was centrifuged for 10 min at 3000 rpm to remove cell debris, and subsequently filtered through a 0.45 μm filter.

The recombinant antibodies in the supernatants were then precipitated with Protein A Sepharose® Fast Flow beads (GE Healthcare, 17-1279-03). 30 mL of the supernatants were mixed with 100 μL Protein A Sepharose® Fast Flow beads and the mixtures were incubated in 50-mL tube for 2 hours at 4° C. under rotation. The mixtures were centrifuged at 3000 rpm for 10 min to remove the supernatant. The remaining beads were washed with PBS at a PBS: beads (v/v) ratio of 20:1. The precipitated antibodies were eluted with 0.1 M glycine (pH 2.5) at a glycine buffer: beads (v/v) ratio of 5:1. The eluates were collected in tubes containing 1M Tris buffer (pH 9.0) at a volume of 1/10 elution volume. The final eluates were dialyzed against PBS buffer. Each dialyzed elates contains purified recombinant antibody 1D2, AMG203 and MOR103, respectively.

Figure 1B:
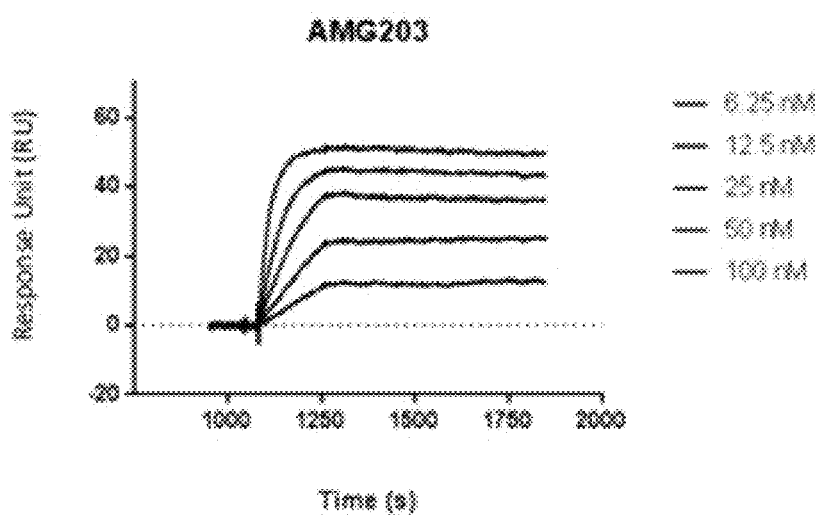
Figure 1C:
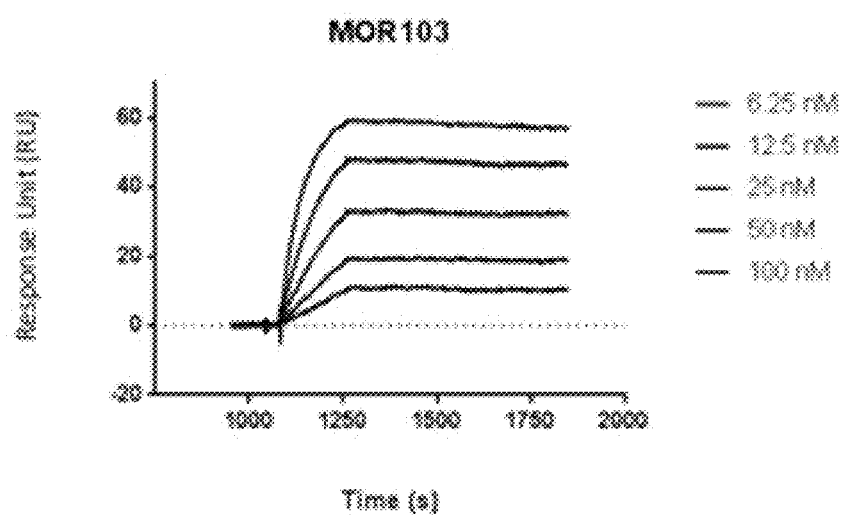

Example 2: Characterization of Recombinant Anti-GM-CSF Antibodies (i) Binding Affinity of ID2 to Human GM-CSF The kinetic binding analysis of anti-GM-CSF antibodies to recombinant human GM-CSF (rhGM-CSF) was determined by Surface plasmon resonance (SPR) using the Biacore 3000 instrument (GE Healthcare). Goat anti-human IgG (5 μg/mL) (SouthernBiotech) was stabilized in 10 mM acetate buffer, pH 4.5, and immobilized on an EDC/NHS pre-activated carboxymethylated dextran 5 (CM5) sensor chip (GE Healthcare) through amine coupling kit (GE Healthcare). HBS-EP buffer (HBS; 10 mM HEPES, 150 mM NaCl, 3 mM EDTA, 0.005% surfactant Tween-20, pH 7.4) (GE Healthcare) was used as running buffer. 1D2, AMG203 and MOR103 were respectively captured on the CM5 sensor chip by goat anti-human IgG. CM5 sensor chip coated only with goat anti-human IgG was used as reference chip. rhGM-CSF (Biolegend) was injected over the mAb-coated CM5 sensor chip and reference chip at different concentrations. The flow rate was 30 μl/min. Triplicate blank injections and duplicate injections of the 12.5 nM rhGM-CSF were included to account for any drift and to ensure assay reproducibility. Injection time and dissociation time were 180 and 600 seconds. Data were fitted to a 1:1 model using the Biacore 3000 evaluation software. FIGS. 1A-1C shows the binding curves obtained by passing different concentrations of rhGM-CSF protein over anti-GM-CSF mAbs immobilized on the CM5 sensor chip. For 1D2, 0, 1.5625, 3.125, 6.25, 12.5, 25 nM of rhGM-CSF were used in the assay. For AMG203 and MOR103, 0, 6.25, 12.5, 25, 50, 100 nM of rhGM-CSF were used in the assay. Antibody-binding kinetic rate constants (Ka and Kd), as well as the equilibrium dissociation constant (KD=Kd/Ka), are shown in Table 4. The 1D2 antibody has a lower $K_D$ value than that of AMG203 and MOR103, indicating 1D2 antibody has higher affinity to rhGM-CSF compared to AMG203 and MOR103.

TABLE 4

Binding Affinity of 1D2 to GM-CSF Relative to AMG203 and MOR103

| Antibody | Ka (1/Ms) | Kd (1/s) | $K_D$ (M) |
| --- | --- | --- | --- |
| 1D2 | $6.43 \times 10^6$ | $7.48 \times 10^{-5}$ | $6.43 \times 10^{-11}$ |
| AMG203 | $2.96 \times 10^5$ | $4.77 \times 10^{-5}$ | $6.2 \times 10^{-10}$ |
| MOR103 | $1.69 \times 10^5$ | $6.19 \times 10^{-5}$ | $3.66 \times 10^{-10}$ |

(ii) Inhibition of GM-CSF Induced STAT5 Phosphorylation in Human PBMCs by ID2

Figure 2A:
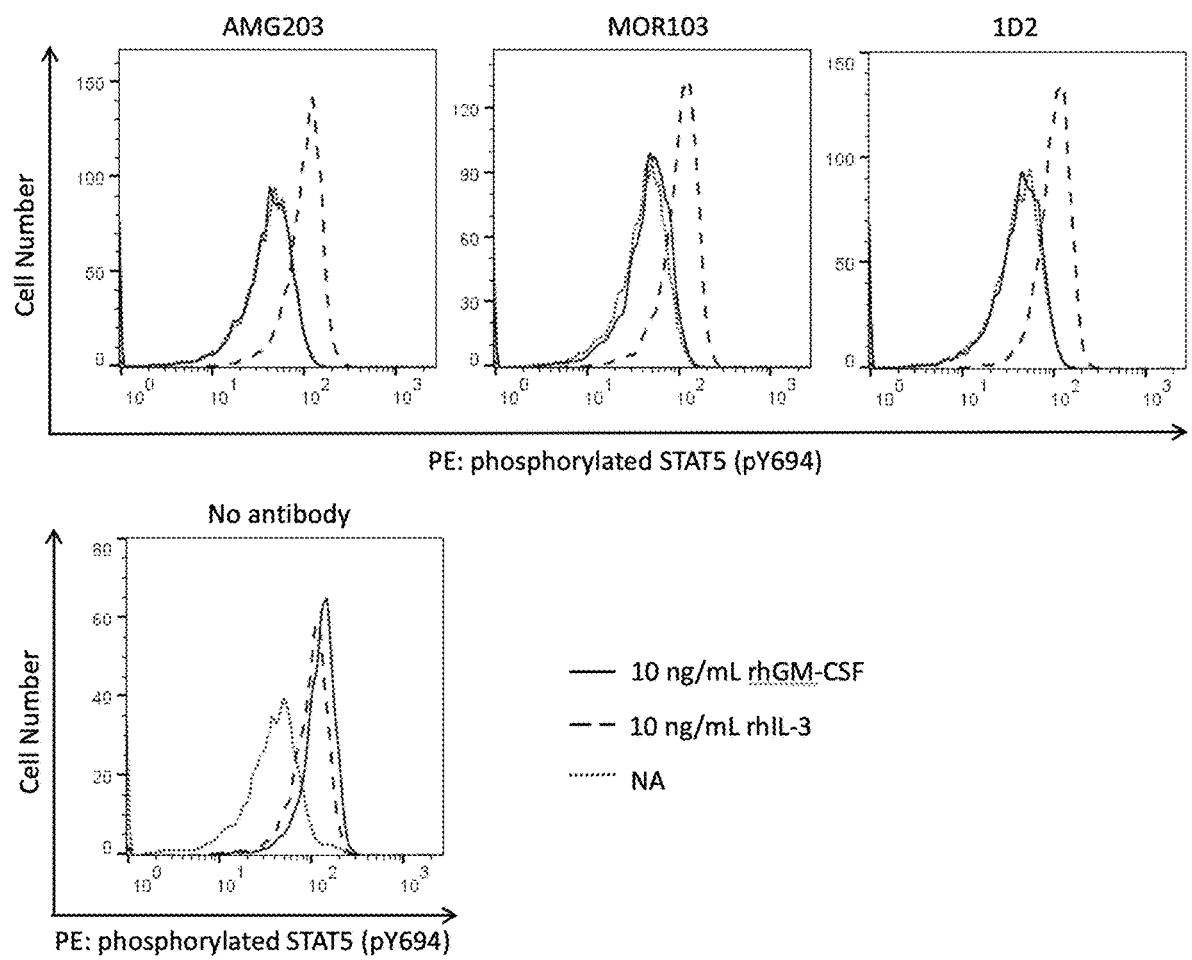
FIG. 2A include flow cytometry charts showing antibody 1D2 inhibits GM-CSF-induced phosphorylation of STAT5 in human peripheral blood mononuclear cells (PBMCs).
Figure 2B:
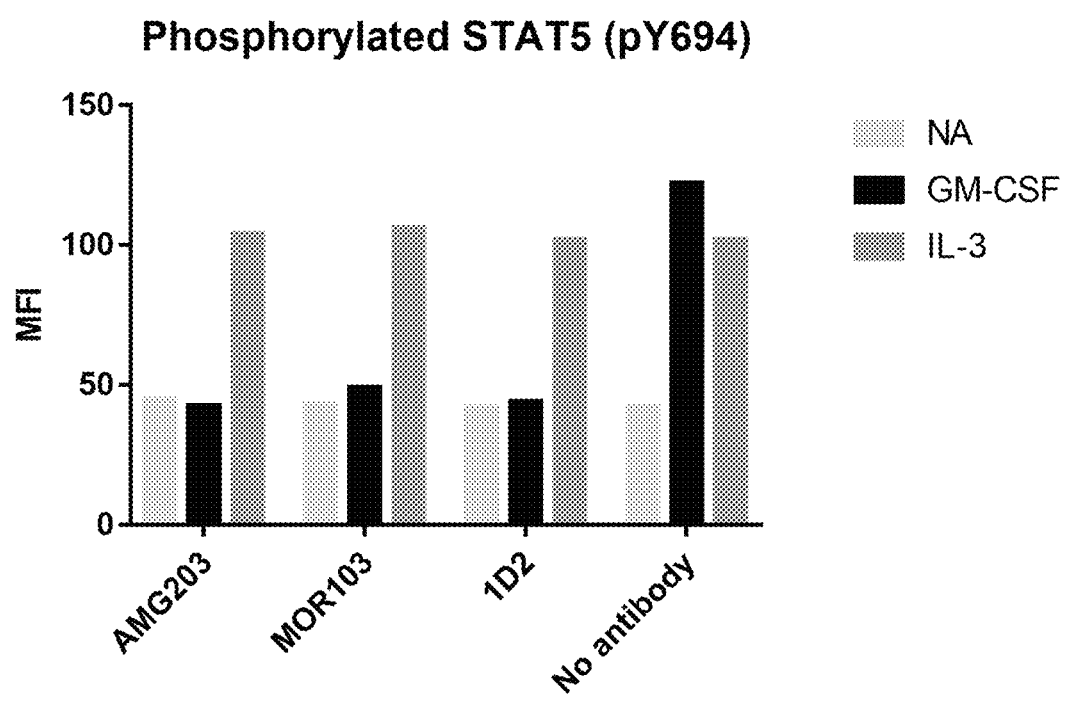
FIG. 2B is a chart showing the mean florescence intensity of the flow cytometry charts in FIG. 2A.

GM-CSF is capable of inducing phosphorylation of STAT5 in human peripheral blood mononuclear cells (PBMCs), which can be inhibited by GM-CSF neutralizing antibodies. The ability of 1D2, AMG203 and MOR103 to inhibit GM-CSF induced phosphorylation of STAT5 in PBMCs was measured. Freshly isolated human PBMCs were stimulated with 10 ng/mL rhIL-3 or 10 ng/mL rhGM-CSF in the presence or absence of 2 g/mL anti-GM-CSF antibody as indicated. After stimulation, PBMCs were stained for cell surface CD14 with anti-CD14-FITC antibody (BD Biosciences). Cells were then fixed in fixation buffer and permeabilized in perm III buffer (BD Biosciences). After permeabilization, intracellular phospho-STAT5 was stained with anti-phosphorylated Stat5 (pY694) antibody. The cells were analyzed by flow cytometry for quantification of phosphorylated Stat5. FIGS. 2A-2B illustrates the flow cytometry analysis of inhibition of phospho-STAT5 signaling by anti-GM-CSF antibodies. In the absence of anti-GM-CSF antibody, rhGM-CSF and rhIL-3 both induced robust STAT5 phosphorylation (pY694) in human PBMCs. Antibody 1D2 completely abolished rhGM-CSF-induced STAT5 phosphorylation in human PBMCs. AMG203 and MOR103 also blocked rhGM-CSF-induced STAT5 phosphorylation in PBMCs. In contrast, 1D2 did not neutralize the bioactivity of IL-3, indicating that 1D2 specifically inhibited GM-CSF. The above results indicated 1D2 exhibits strong GM-CSF neutralizing activity in human PBMCs. Table 11 is a quantification of MFIs in the flow cytometry charts.

TABLE 11

Mean Fluorescence Intensity of Anti-GM-CSF Antibodies on Neutralizing GM-CSF and IL-3

| | NA | GM-CSF | IL-3 |
| --- | --- | --- | --- |
| AMG203 | 44.8 | 42.6 | 104 |
| MOR103 | 43.2 | 48.9 | 106 |
| 1D2 | 42.1 | 44.1 | 102 |
| No antibody | 42.4 | 122.0 | 102 |

(iii) Inhibition of GM-CSF Dependent TF-1 Cell Proliferation by ID2

Figure 3:
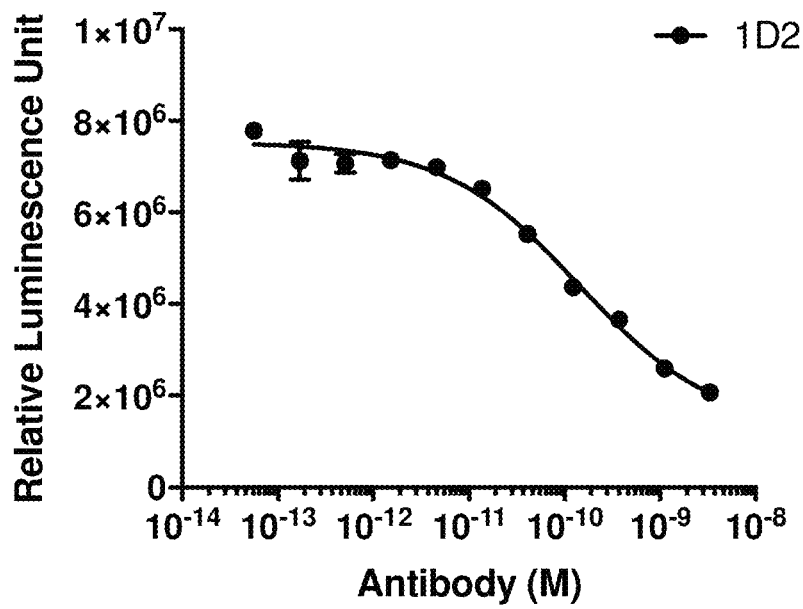
FIG. 3 is a chart showing exemplary antibody 1D2 inhibits GM-CSF-induced TF-1 cell proliferation in a dose dependent manner.

GM-CSF is capable of inducing cell proliferation of human erythroleukemia cell lime TF-1. The proliferative property of GM-CSF to TF-1 cells can be inhibited by GM-CSF neutralizing antibodies. The ability of 1D2 to block the proliferative effect of rhGM-CSF in TF-1 cells was measured. TF-1 Cells (ATCC, CRL-2003) were obtained from Bioresource Collection and Research Center (BCRC, Taiwan). In the proliferation assay, TF-1 cells were seeded in 96 wells at $1.5 \times 10^4$ cells per well in 100 μl of RPMI. Recombinant human GM-CSF (rhGM-CSF, 0.5 ng/mL, Biolegend) were pre-incubated with various amounts of 1D2 for 25 min in 100 μl RPMI. The mixture was then added to seed TF-1 cells. TF-1 cell proliferation was measured 72 hours post stimulation using CellTiter-Glo assay (Promega). As shown in FIG. 3, 1D2 inhibited the proliferation of TF-1 induced by rhGM-CSF in a dose-dependent manner. Antibody 1D2 showed a potent inhibition of GM-CSF induced TF-1 cell proliferation at a half maximal concentration of 1.436×10−10 M, which is a sub-nano molar concentration. The above results indicated that 1D2 can effectively inhibit biological activity of GM-CSF.

(iv) Inhibition of GM-CSF Induced CCL17 Secretion in Human PBMCs by ID2

Figure 4:
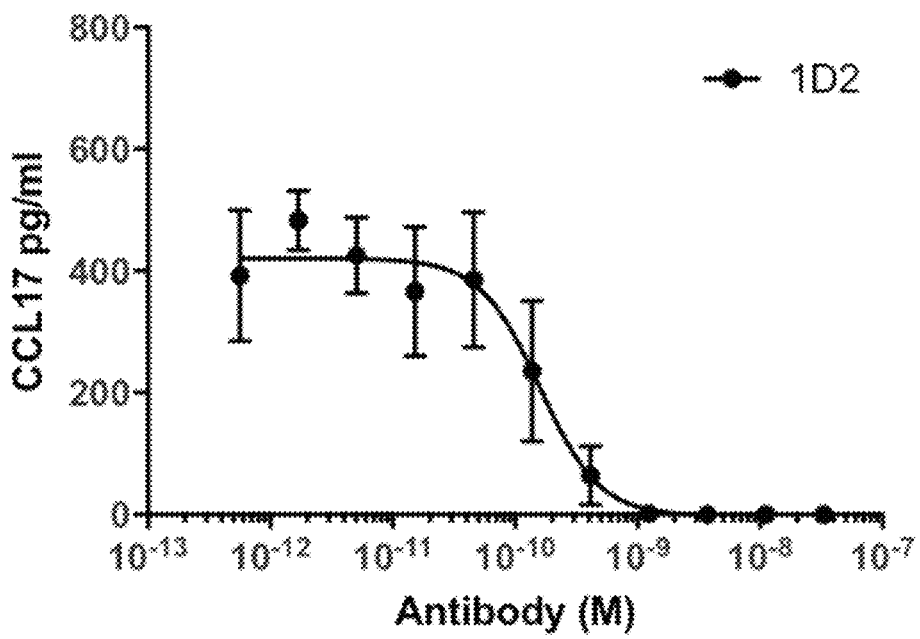
FIG. 4 is a chart showing exemplary antibody 1D2 inhibits GM-CSF-induced CCL17 secretion from PBMCs in a dose dependent manner.

One of the various biological activities of GM-CSF is to drive the production of CCL17 chemokine in human monocytes/macrophages, which is an important biomarker for the progression of GM-CSF associated inflammatory diseases. CCL17 has been identified as the primary downstream effector chemokine of various GM-CSF associated inflammatory diseases. The effect of 1D2 to inhibit GM-CSF induced secretion of CCL17 in human PBMCs was investigated. Human PBMCs were isolated from healthy volunteers using Ficoll-Paque method. $2\times10^5$ isolated human PBMCs were stimulated with 1 ng/mL rhGM-CSF preincubated various amounts of antibody 1D2 for 24 hours. The supernatant of PBMC culture was collected and CCL17 secretion by PBMCs was analyzed by ELISA. As shown in FIG. 4, 1D2 potently inhibited CCL17 secretion in rhGM-CSF stimulated PBMCs in a dose dependent manner. The IC50 of 1D2 was determined as $1.586\times10-10$ M, which was similar to the concentration required for half maximal inhibition of TF-1 cell proliferation. Taken together, these data indicate that 1D2 effectively neutralizes GM-CSF activity in a biological context highly relevant to GM-CSF associated inflammatory diseases, for example Kawasaki disease.

Example 3: SDR Mutant Clones of Antibody 1D2

(1) Identification of SDR Mutant Clones of Antibody ID2 with Sufficient Binding Affinity to Human GM-CSF Determining the residues that are important for the molecular activity of an antibody is a topic of can help to fine-tune the antibody's function for binding affinity and epitope specificity. Some of the residues in the CDRs are essential for epitope binding affinity and/or specificity. A number of computational methods were developed to detect these functional residues, generally known as 'specificity-determining resides' (SDRs). In the present disclosure, heavy chain and light chain sequences of antibody 1D2 were analyzed. A 3D model of antibody 1D2 was computationally built up and analyzed. Based on the analysis, 7 amino acid residues in $V_H$ and 3 amino acid residues in $V_L$ were selected as the SDRs. The residues are labeled $X_1$ to $X_{10}$ for the ease of reference. The SDRs on $V_H$ are: Heavy chain D31 (HD31)($X_1$), HK32 ($X_2$), HK54($X_3$), HR100 ($X_4$), HY102 ($X_5$), HY103 ($X_6$) and HQ105 ($X_7$). The SDRs on $V_L$ are Light chain V32 (LV32)($X_8$), LP94 ($X_9$) and LV95 ($X_{10}$). The SDRs were subsequently mutated by site-directed mutagenesis to other amino acids to generate mutant $V_H$ or $V_L$ clones. HEK293 cells were co-transfected with a vector encoding a mutant $V_H$ paired with a vector encoding a wild type $V_L$ or a vector encoding a wild type $V_H$ paired with a vector encoding a mutant $V_L$. The antibody clones were harvested from the culture medium. The binding affinity of each antibody clone to human GM-CSF was tested by ELISA. The ELISA was done according to the following procedures. ELISA plate was coated with 50 μl of rhGM-CSF at 1 μg/mL. The plate was washed with 200 μl PBST for three times, followed by blocking with 1% BSA for 1 hour at room temperature. The antibody clones to be tested were diluted at 1:12000. 100 μl of the diluted antibodies were added to the cell at 100 l/well. The plate was incubated at room temperature for 1 hour. The plate was then washed and incubated with 1:5000 diluted goat-anti-human secondary antibody conjugated with HRP at room temperature for one hour. The ELISA assay was developed with 100 μl developing buffer containing $H_2O_2$-Amplx Red per well in the dark for 5 min and the fluorescence intensity was read at Ex.530/Em.590 nm, with cutoff at 570 nm. The Unit Binding Activity (UBA) of each sample was calculated as the fluorescence signal/antibody clone dilution factor. The percentage of binding affinity of mutant antibody clones to GM-CSF is calculated by (UBA of each mutant clone/UBA of 1D2)*100%.

A set of antibodies with SDR mutations retain more than 40% of the binding affinity to human GM-CSF compared to 1D2 were identified to form a library of antibody 1D2 variants that's capable of binding to GM-CSF. Table 5 shows the SDRs in the CDRs (SDRs shown in bold face) and the mutations that retain the binding affinity of the antibodies to human GM-CSF. The binding affinity of various mutant antibody clones is shown in Table 2.

TABLE 5

Variations in CDRs

| | | |
|---|---|---|
| HC CDR1 | GYTFTDKY (SEQ ID NO: 5)<br>GYTFTX$_1$X$_2$Y (SEQ ID NO: 11) | X$_1$ can be: D, E, S, P, G, A, V, N, Q, C, W, R, T, L<br>X$_2$ can be: K, V, L, E, P, S, T, C, D, R, H, A, F, Q, N |
| HC CDR2 | INPKSGGT (SEQ ID NO: 6)<br>INPX$_3$SGGT (SEQ ID NO: 12) | X$_3$ can be: K, L, M, E, H, S, V, N, C, F, P, W, G, A, I, R, T Q |
| HC CDR3 | ARGRDYYDQGAADL (SEQ ID NO: 7)<br>ARGX$_4$DX$_5$X$_6$DX$_7$GAADL (SEQ ID NO: 13) | X$_4$ can be: R, V, S, A, C, L, P, I, T, G, M, E, Q<br>X$_5$ can be: Y, I, L, W, F, T, V, A, G, N, Y, S<br>X$_6$ can be: Y, N, P, S, K, R, G, W, D, Q, L, H, F, A, T, V, M<br>X$_7$ can be: Q, S, T, M, N, G, V, L, E, W |
| LC CDR1 | QGINSV (SEQ ID NO: 8)<br>QGINSX$_8$ (SEQ ID NO: 14) | X$_8$ can be: V, L, G, E, R, F, P, H, Y |
| LC CDR2 | AAS (SEQ ID NO: 9) | |
| LC CDR3 | QQYYSPVRT (SEQ ID NO: 10)<br>QQYYSX$_9$X$_{10}$RT (SEQ ID NO: 15) | X$_9$ can be: P, R, N, C<br>X$_{10}$ can be: V, C, D. L, E, P, R |

The binding affinity of several mutant antibody clones was tested by Biacore, as shown in Table 6 and Table 7 below:

TABLE 6

| Binding Affinity of 1D2 Variants | | | | | | |
|---|---|---|---|---|---|---|
| | ka (1/Ms) | kd (1/s) | Rmax (RU) | KA (1/M) | KD (M) | Chi2 |
| WT | 1.75E+06 | 1.73E−04 | 40.7 | 1.01E+10 | 9.90E−11 | 0.524 |
| 103N | 1.67E+06 | 6.69E−04 | 44 | 2.50E+09 | 4.00E−10 | 0.531 |
| 103N/32R | 6.40E+05 | 2.70E−03 | 42.3 | 2.37E+08 | 4.22E−09 | 0.234 |
| 103R | 1.38E+06 | 5.70E−04 | 43.6 | 2.42E+09 | 4.14E−10 | 0.59 |
| 103R/32R | 9.98E+05 | 2.41E−03 | 45.5 | 4.14E+08 | 2.42E−09 | 4.26 |
| 54G | 1.30E+06 | 4.48E−04 | 35.3 | 2.89E+09 | 3.46E−10 | 0.156 |
| 54G/32R | 1.03E+06 | 1.97E−03 | 37.9 | 5.23E+08 | 1.91E−09 | 0.375 |

TABLE 7

| Binding Affinity of 1D2 Variants | | | | |
|---|---|---|---|---|
| | Gator (pro) Coating Ag | Gator Coating Ag | Gator Coating Ab | Biacore |
| WT | 1.57E−12 | 1.76E−11 | 1.77E−10 | 1.62E−10 |
| Y103N/V32R | 5.84E−12 | 2.01E−11 | 1.44E−09 | 3.36E−09 |
| Y103R/V32R | 2.8E−12 | 3.09E−11 | 4.14E−09 | 7.76E−09 |
| K54G/V32R | 7.46E−13 | 2.22E−11 | 9.29E−10 | 1.50E−09 |

(ii) Inhibition of GM-CSF Dependent TF-1 Cell Proliferation by SDR Mutant Antibody Clones of Antibody 5D2

Figure 5A:
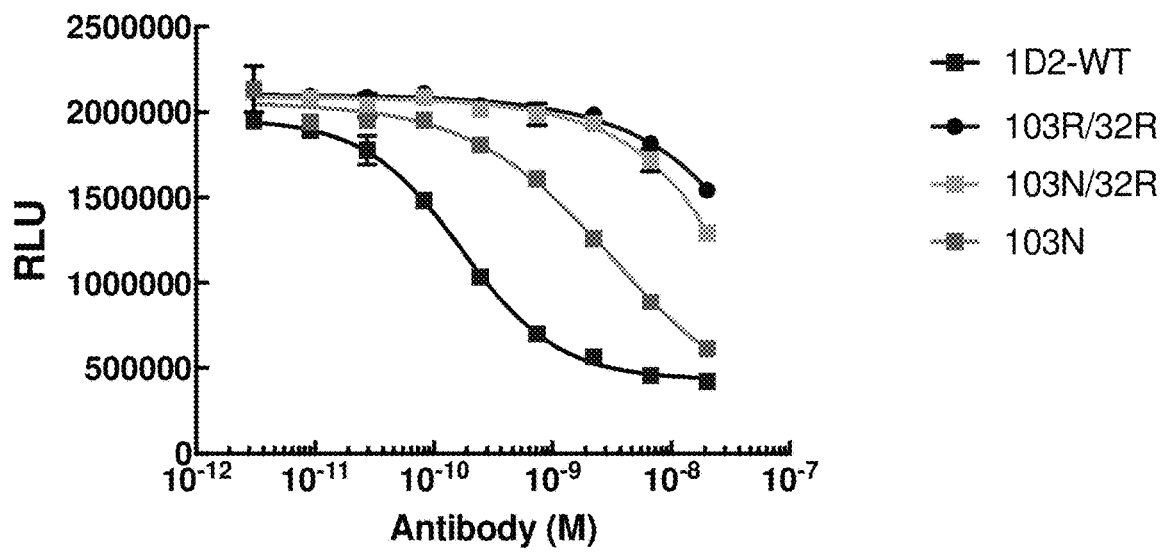
FIGS. 5A-5B are charts showing SDR mutant antibodies of 1D2 are able to inhibit GM-CSF TF-1 cell proliferation, but the effect is less potent than wild type 1D2 antibody.
Figure 5B:
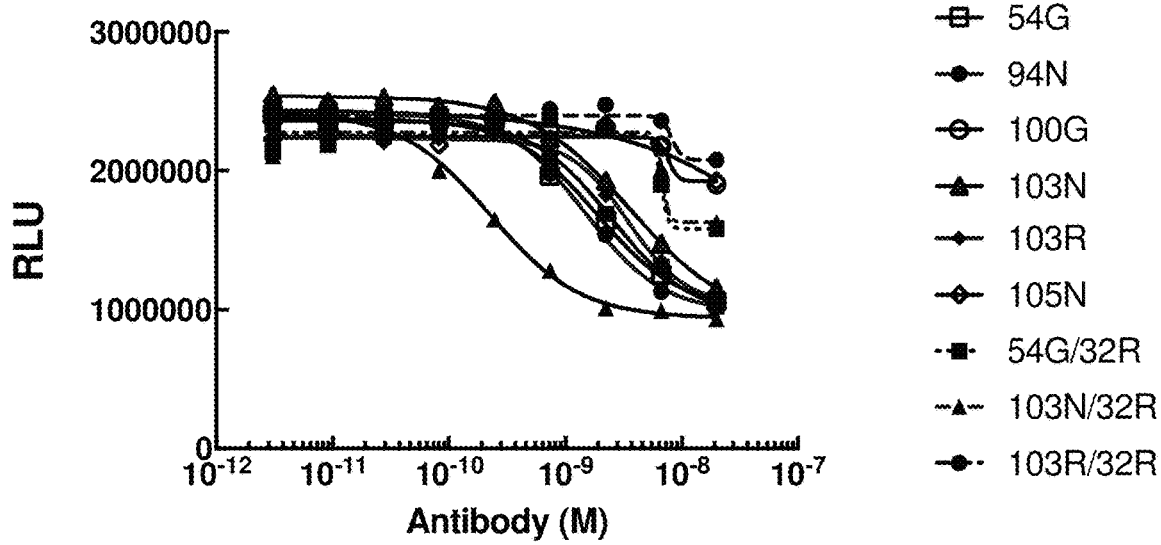
Figure 6A:
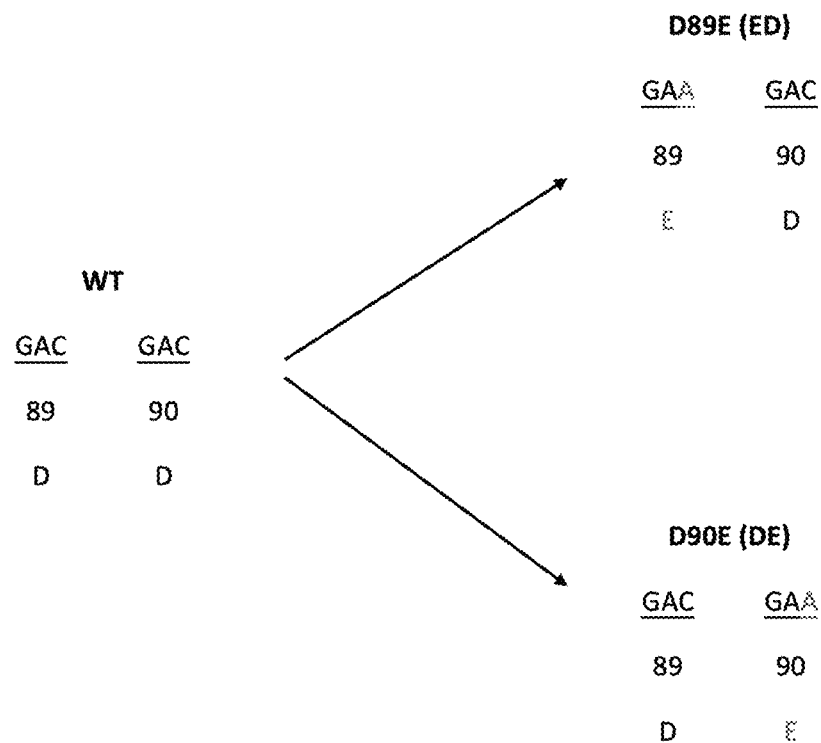
FIGS. 6A-6I are charts showing characteristics of the D89E and D90E mutants as compared to 1D2.
Figure 6B:
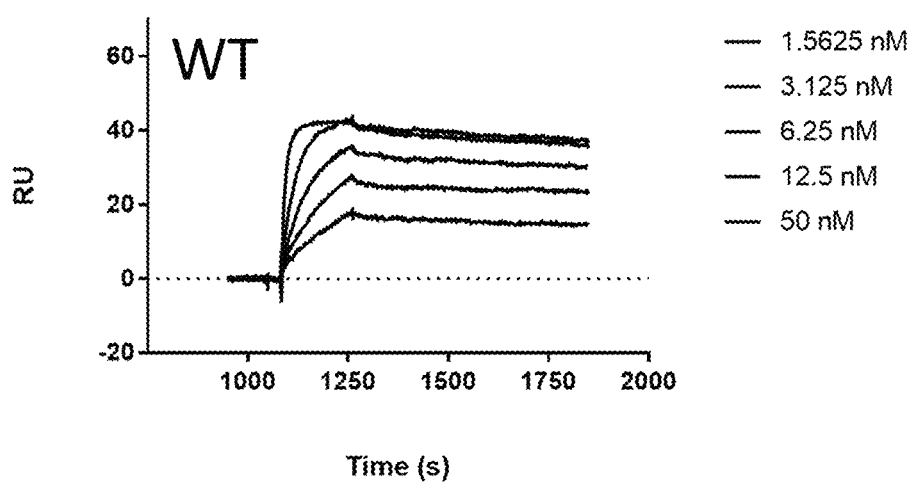
Figure 6C:
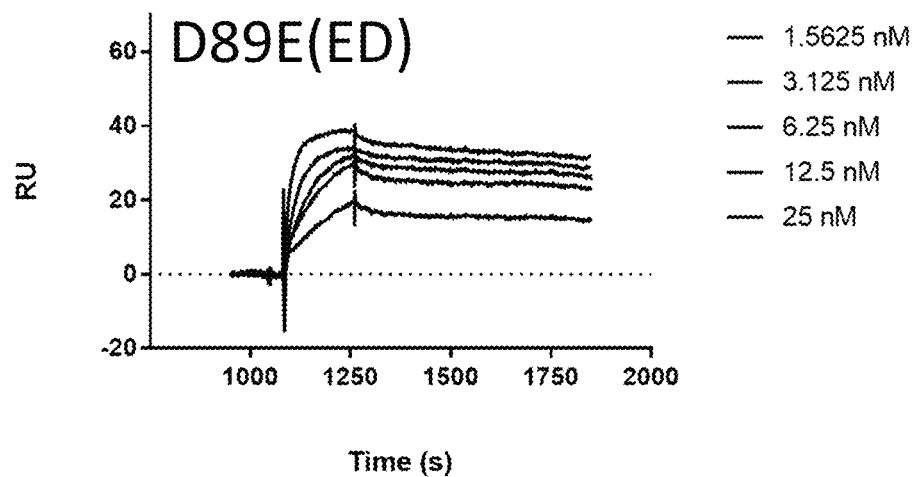
Figure 6D:
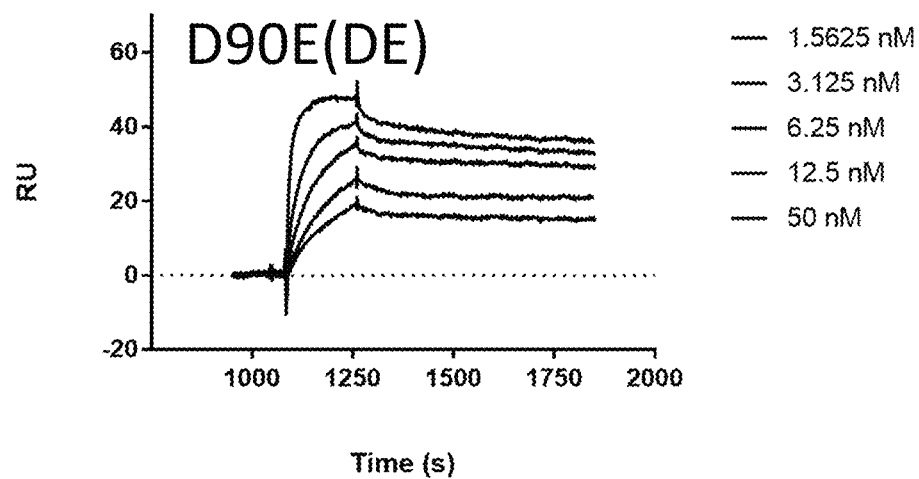
Figure 6E:
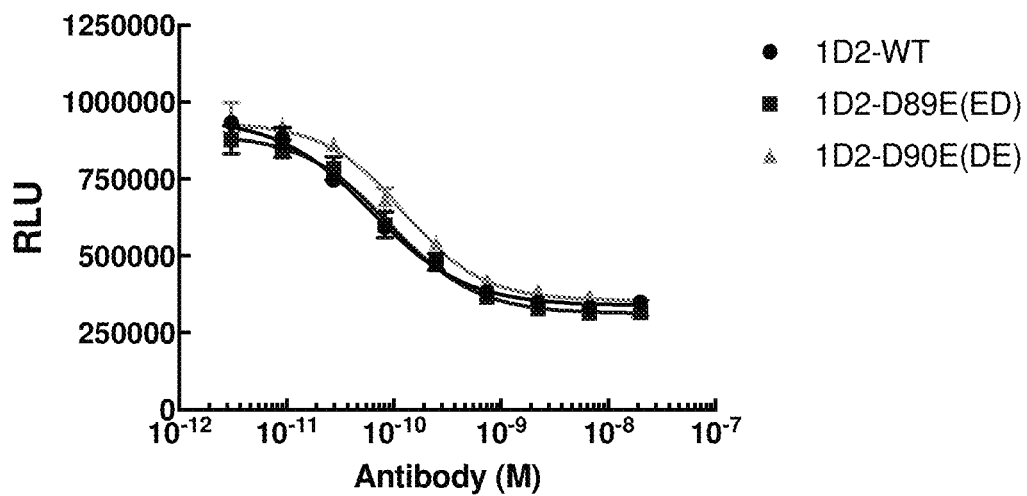
Figure 6F:
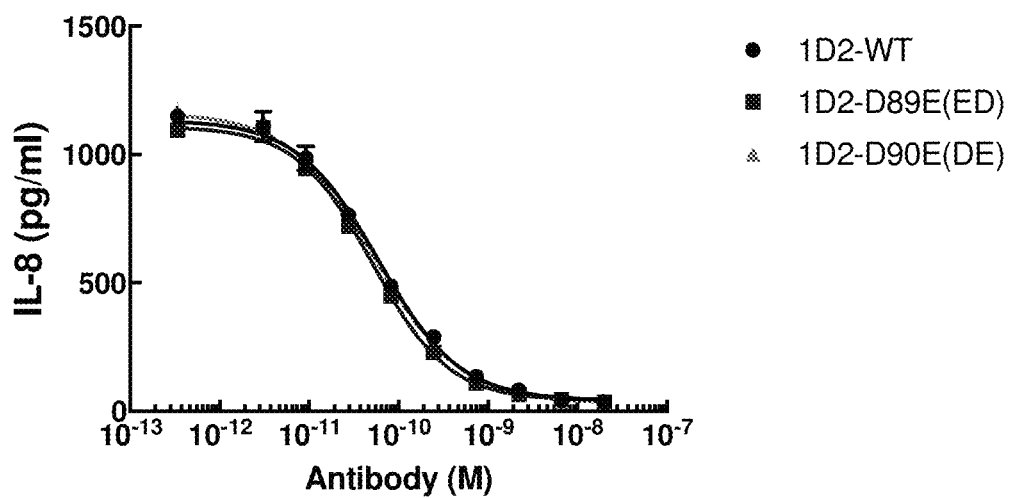
Figure 6G:
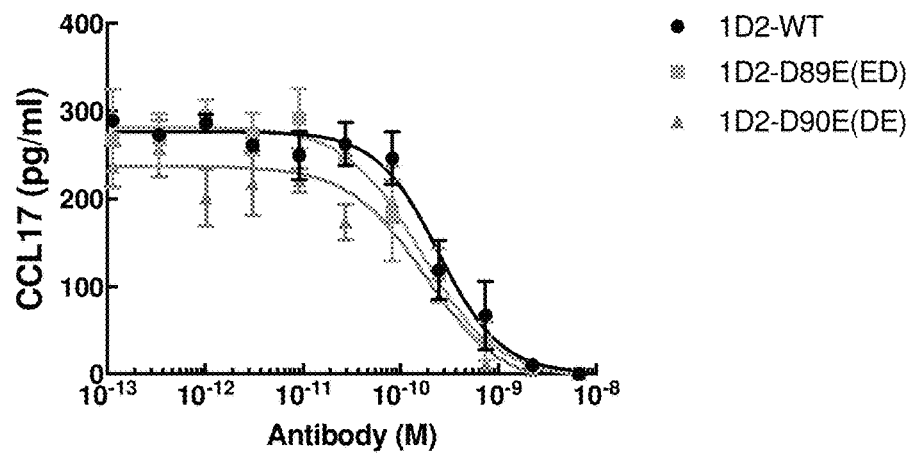

The ability of several selected SDR mutant antibody clones to inhibit GM-CSF induced TF-1 cell proliferation was tested. FIGS. 5A and 5B show that the SDR mutant antibodies inhibited TF-1 cell proliferation, but at a higher $IC_{50}$ value. The $IC_{50}$ of the antibodies tested in FIGS. 5A and FIG. 5B are shown in Table 8.

TABLE 8

| IC50 Values of 1D2 and Variants Thereof | | | | | |
|---|---|---|---|---|---|
| | 1D2-WT | 103N | 103N/32R | 103R/32R | 1D2-WT |
| IC50 (M) | 1.712e−10 | 3.411e−9 | ~0.000864 | ~0.001708 | 2.281e−10 |
| | 32R | 54G | 94N | 100G | 103N |
| IC50 (M) | 2.483e−09 | 1.872e−09 | 1.487e−09 | ~3.189 | 3.605e−09 |
| | 103R | 105N | 54G/32R | 103N/32R | 103R/32R |
| IC50 (M) | 3.467e−09 | 7.666e−09 | 6.62e−09 | ~6.827e−09 | ~8.194e−09 |

Example 4. Removal of DD Motif Liability from Antibody 1D2 Heavy Chain Framework Region As the lead antibody for further development, antibody ID2 needs to be stable for production. The amino acid sequence of 1D2 was analyzed for liabilities that would decrease antibody stability. A DD motif was identified in the heavy chain framework region at amino acid residues 89 and 90. Spontaneous isomerization of Asp residues of a DD motif could occur during production, storage or treatment, leading to loss of function or potency of the antibody. In order to eliminate the liability caused by the DD motif, aspartic acid can be mutated to glutamic acid, which is functionally similar to aspartic acid. Accordingly, two isomerization site mutants of antibody 1D2 (D89E and D90E mutants) were constructed, as shown in FIG. 6A. The binding affinity of the D89E (ED mutant) and D90E (ED mutant) mutants to human GM-CSF were measured by Biacore. FIGS. 6B-6D show the binding curve of WT (1D2), ED mutant and DE mutant. Table 9 shows the Antibody-binding kinetic rate constants (Ka and Kd), as well as the equilibrium dissociation constant (KD=Kd/Ka) of 1D2, ED mutant and DE mutant.

TABLE 9

| Binding Affinity of FR Variants Relative to 1D2 | | | |
|---|---|---|---|
| Loading Sample ID | KD (M) | kon (1/Ms) | kdis (1/s) |
| ID2 wildtype | 9.90E−11 | 1.75E+06 | 1.73E−04 |
| ID2-D89E (ED) | 7.32E−11 | 2.58E+06 | 1.88E−04 |
| ID2-D90E (DE) | 1.14E−10 | 1.74E+06 | 1.98E−04 |

The ability of ED and DE mutant antibodies to block the proliferative effect of rhGM-CSF in TF-1 cells was measured and compared to wild type antibody 1D2. In the proliferation assay, TF-1 cells were seeded in 96 wells at $1.5\times10^4$ cells per well in 100 µl of RPMI. Recombinant human GM-CSF (rhGM-CSF, 0.5 ng/mL, Biolegend) were pre-incubated with various amounts of antibody 1D2, ED mutant antibody, or DE mutant antibody for 25 min in 100 µl RPMI. The mixture was then added to TF-1 cells. TF-1 cell proliferation was measured 72 hours post stimulation using CellTiter-Glo assay (Promega). As shown in FIG. 6E, antibodies D89E (ED) and D90E (DE) showed potent inhibition of GM-CSF induced TF-1 cell proliferation at IC50 of 9.714×10−11 M, 1.231×10−10 M, respectively. Wild type antibody 1D2 inhibited TF-1 cell proliferation at IC50 of 6.312×10−11 M. The data indicates that the D89E and D90E mutation did not affect the biological function of the antibody. The mutant antibodies are able to exert GM-CSF neutralizing effect at comparable level of wild type antibody 1D2.

Another function of GM-CSF is to induce IL-8 production in U937 cells. U-937 cells were maintained in suspension culture in RPMI-1640 supplemented with 10% heat-inactivated FBS and 1% penicillin/streptomycin at 37° C. in a humidified atmosphere of 5% C02. U-937 cells were seeded in 100 µl assay medium ($2\times10^5$ cells/well) in 96 wells. Next, rhGM-CSF (1 ng/mL) were pre-incubated with indicated antibodies for 25 min in 100 µl of RPMI assay medium, then added to 100 µl assay medium with $2\times10^5$ U-937 cells. After 24 hours incubation, culture supernatant was collected, and IL-8 concentration was measured using ELISA method according to the manufacturer's instruction. Data were fitted for half-maximal inhibition of IL-8 production by a non-linear regression curve fit using GraphPad Prism7. As shown in FIG. 6F, the $IC_{50}$ of wild type antibody 1D2, ED mutant and DE mutant in inhibition of IL-8 secretion in U937 cells were 5.94×10−11 M, 5.10×10−11 M, and 5.40×10−11 M, respectively. This data indicates that mutant antibodies are able to exert GM-CSF neutralizing effect at comparable level of wild type antibody 1D2.

Further, the ability of ED and DE mutant antibodies to inhibit GM-CSF induced CCL17 production in PBMCs were measured and compared to wild type antibody 1D2. Human PBMCs were isolated from healthy volunteers using Ficoll-Paque method. $2\times10^5$ isolated human PBMCs were stimulated with 1 ng/mL rhGM-CSF preincubated with various amounts of antibody 1D2, ED mutant antibody or DE mutant antibody, and incubated for 24 hours. The supernatant of PBMC culture was collected and CCL17 secretion by PBMCs was analyzed by ELISA. As shown in FIG. 6G, ED and DE mutant antibodies potently inhibited CCL17 secretion in rhGM-CSF stimulated PBMCs in a dose dependent manner. The $IC_{50}$ of wild type antibody 1D2 and ED mutant in inhibition of CCL17 secretion from PBMCs were 7.14×10−11 M and 5.43×10−11 M, respectively. This data indicates that ED and DE mutant antibodies are able to exert GM-CSF neutralizing effect at comparable level of wild type antibody 1D2.

Figure 6H:
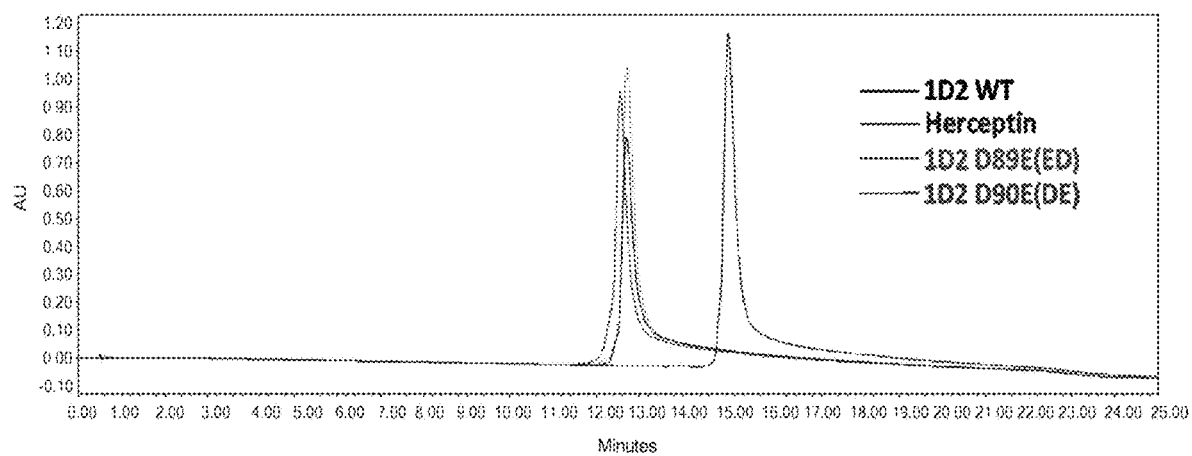

Next, the heterogeneity of 1D2, ED and DE mutant antibodies were analyzed by Hydrophobic interaction chromatography (HIC). HIC separates proteins according to differences in their surface hydrophobicity by utilizing a reversible interaction between the proteins and the hydrophobic surface of a HIC resin. The ultra performance liquid chromatography (UPLC) system consists of an Acquity UPLC H-class bio system with a quaternary UPLC pump and a quaternary solvent manager (QSM), an automatic sample injection device (SM) equipped with a 50 µl sample loop and a photodiode array detector (Waters). 10 g of each sample was injected and separation was achieved by using a TSKgel Butyl NPR (TOSOH, 4.6 mm ID×3.5 cm) at 35° C. The mobile phase consisted of two buffers: buffer A (2M ammonium sulfate in 25 mM sodium phosphate, pH 7.0) and buffer B (25 mM sodium phosphate, pH 7.0). The flow rate was 0.5 mL/min and the total running time was about 25 min. Absorbance was monitored at 214 and 280 nm. Furthermore, a UV spectrum was recorded from 400-210 nm using a diode-array detector. Chromatograms were processed and calculated by the Empower software (v3.0, Waters). As shown in FIG. 6H, 1D2, ED and DE mutant antibodies produced peaks at similar retention time as compared to a different antibody, Herceptin, indicating that ED and DE mutant antibodies have similar surface hydrophobicity as wild type antibody 1D2. Moreover, the ED mutant has a reduced level of shoulder species compared to 1D2 and DE mutant, suggesting ED mutant antibody has higher purity. The results indicate that ED mutant has improved biophysical properties for manufacturing and/or storage.

Figure 6I:
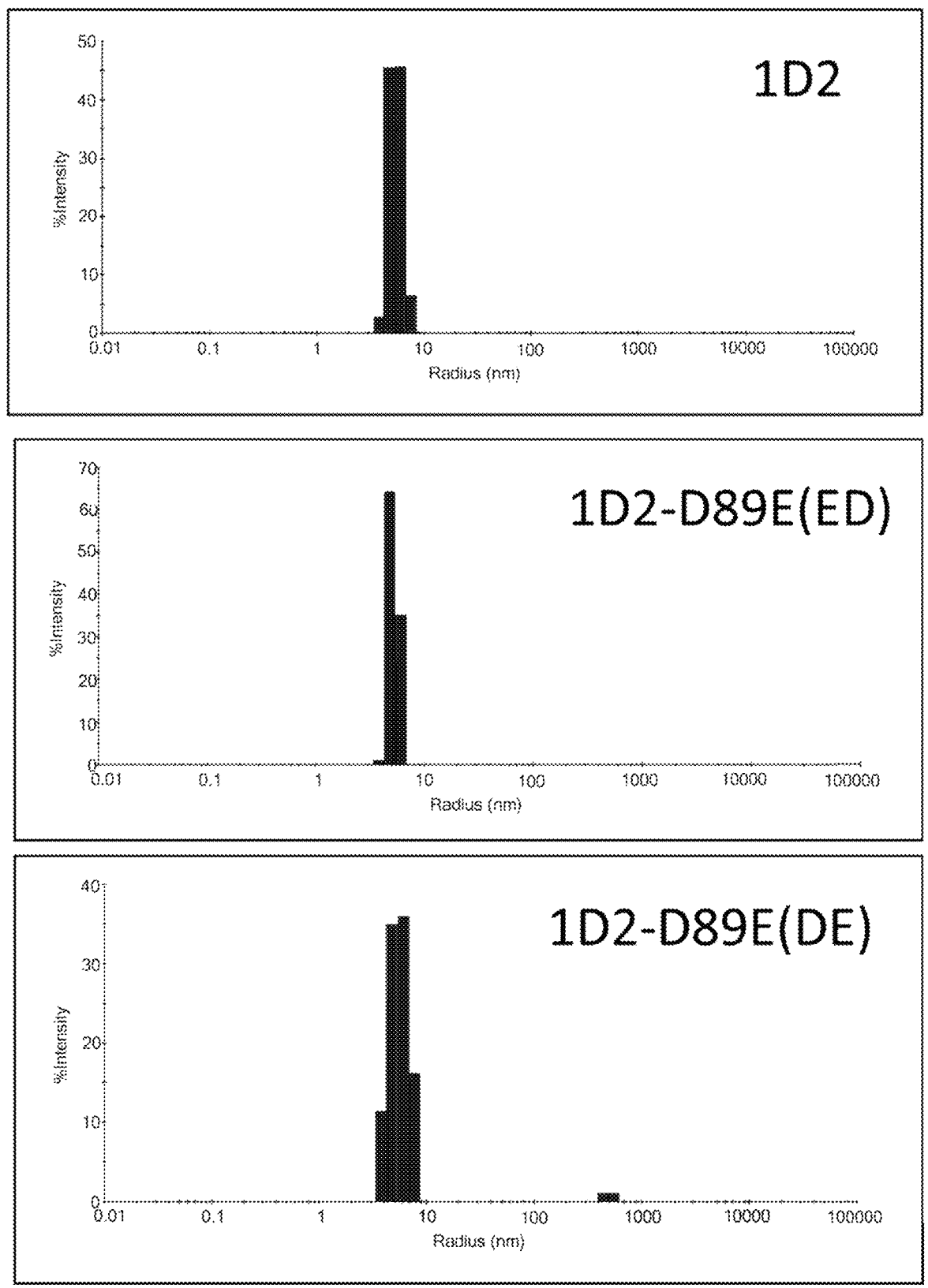

In addition, the aggregation state of purified 1D2, ED and DE mutant antibodies were analyzed by Dynamic light scattering (DLS). DLS analysis was measured using Dyna-Pro NanoStar (Wyatt) at a laser wavelength of 658 nm. Antibodies were diluted to 2 mg/mL with PBS and filtered with a 0.02 µm pore size filter (alumina based membrane) before measurement. 10 µL of sample were transferred into disposable cuvettes and analyzed at 25° C. DYNAMICS software was used to schedule and automate acquisitions with an acquisition time of 5s and 10 acquisitions per measurement for each sample. These instruments are equipped with integral algorithms to automatically determine the Laser Power (%) and Attenuation Level (%) for each measurement in real time. The scattering data were fit (Dynamics software; Wyatt) assuming the scatterers to be Rayleigh spheres. "Radius" is the protein particle diameter, "mass percentage" is the amount of each size fraction in percentage, "PD percentage" is the indicator for antibody polydispersity. The higher the PD percentage, the more polydispersity the sample is. As shown in Table 10 and FIG. 6I, ED mutant has reduced polydispersity percentage compared to 1D2 and DE mutant. This result suggests that the ED mutant is less prone to aggregation than wildtype 1D2, and DE mutant. ED mutant may have improved biophysical properties during development.

TABLE 10

Stability of FR Variants Relative to 1D2

| | Peak 1 | | | Peak 2 | | |
|---|---|---|---|---|---|---|
| Sample | Radius (nm) | PD % | Mass % | Radius (nm) | PD % | Mass % |
| 1D2 | 5.6 | 15.8 | 100 | — | — | — |
| 1D2-D89E(ED) | 5.3 | 12.0 | 100 | — | — | — |
| 1D2-D89E(DE) | 5.7 | 21.2 | 99.9 | 503.6 | 11.8 | 0.1 |

Taken together, the ED and DE mutant antibodies have similar biological function to wild type 1D2 antibody, while the D89E and D90E mutation increases the stability of the antibodies for production and shelf life.

Example 5. Binding Specificity of 1D2, ED and DE Mutant Antibodies

Human and mouse GM-CSF have about 56% homology and are species specific. Rhesus and GM-CSF has 96.5% homologous to human GM-CSF (Hutchinson et al, J Med Virol 2001, 65:561-565, Genbank accession number AY007376). The ability of 1D2, ED and DE mutant antibodies to bind to GM-CSF derived from mouse or rhesus was measured by ELISA. ELISA was performed as followed. Briefly, GM-CSF proteins were coated on the ELISA absorbing plates, then blocked by 1% BSA in PBS. Subsequently, monoclonal antibody 1D2, 1D2-D89E(ED) or 1D2-D90E(DE) were added to plate and incubated at room temperature for one hour. After incubation, the plates were washed three times with TBST and incubated with anti-human kappa light chain conjugated HRP secondary antibodies. Plates were washed three times, TMB peroxidase substrate was added and reactions were stopped by adding 1 N sulfuric acid. Finally, absorbance at 450 nM was measured using an ELISA reader, and GraphPad Prism7 software was used to plot nonlinear regression curve fitting of data points.

Figure 7A:
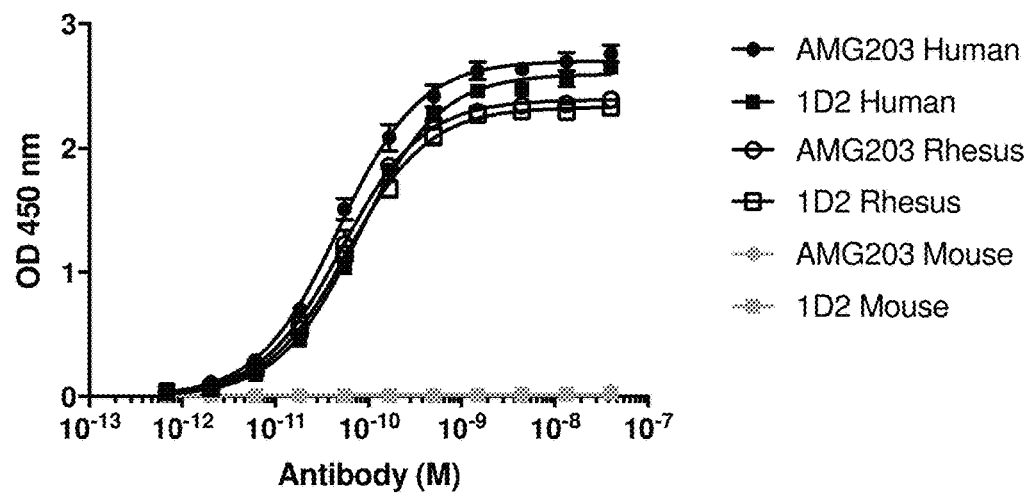
Figure 7B:
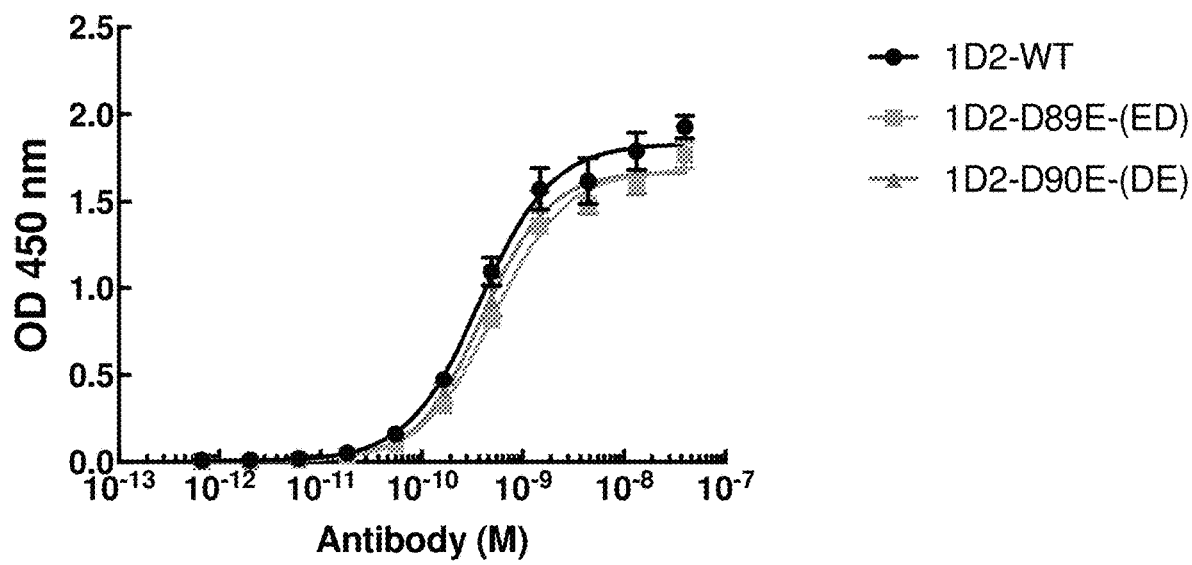
Figure 7C:
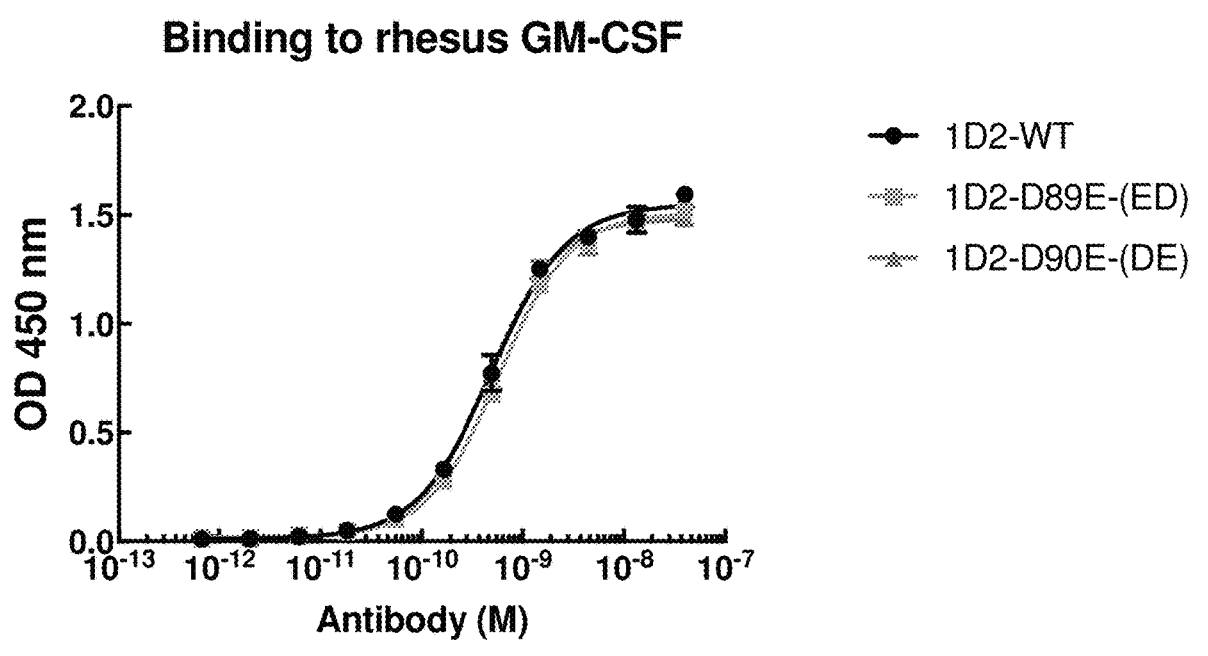

FIG. 7A shows that antibody 1D2 are capable of binding to human GM-CSF and rhesus GMCSF at high affinity but are unable to bind to mouse GM-CSF. Further, the binding ability of ED and DE mutant antibodies to human and rhesus GM-CSF were measured by ELISA. FIGS. 7B-7C show that ED and DE mutant antibodies are able to bind to human and rhesus GM-CSF similarly to wild type antibody 1D2.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An isolated antibody, which binds to granulocyte-macrophage colony-stimulating factor (GM-CSF), wherein the antibody comprises:
   (a) a heavy chain variable domain ($V_H$), which comprises a HC CDR1 of SEQ ID NO: 5, a HC CDR2 of SEQ ID NO: 6, and a HC CDR3 of SEQ ID NO: 7, and a light chain variable domain ($V_L$), which comprises a LC CDR1 of SEQ ID NO: 8, a LC CDR2 of SEQ ID NO: 9, and a LC CDR3 of SEQ ID NO: 10;
   (b) a variant of the antibody set forth in (a), wherein one of HC CDR1, HC CDR2, HC CDR3, LC CDR1, or LC CDR3 is selected from
       (i) HC CDR1 of SEQ ID NO: 21 or 22,
       (ii) HC CDR2 of SEQ ID NO: 23,
       (iii) HC CDR3 of SEQ ID NO: 24, 25, 26 or 27;
       (iv) LC CDR1 of SEQ ID NO: 28,
       (v) LC CDR3 of SEQ ID NO: 29 or 30.

2. The isolated antibody of claim 1, wherein the antibody comprises a $V_H$ comprising the amino acid sequence of SEQ ID NO: 1, 3, or 4, and/or a $V_L$ comprising the amino acid sequence of SEQ ID NO: 2.

3. The isolated antibody of claim 1, wherein the antibody comprises a heavy chain variable domain ($V_H$) that is at least 85% identical to the amino acid sequence of SEQ ID NO: 1, and a light chain variable domain ($V_L$) that is at least 85% identical to the amino acid sequence of SEQ ID NO: 2.

4. The isolated antibody of claim 1, wherein the antibody is a human antibody or a humanized antibody.

5. The isolated antibody of claim 1, wherein the antibody is a full-length antibody or an antigen binding fragment thereof.

6. The isolated antibody of claim 5, wherein the antibody is a full-length antibody, which is an IgG molecule.

7. The isolated antibody of claim 1, wherein the antibody is conjugated to a detectable label.

8. A pharmaceutical composition comprising an isolated antibody of claim 1, and a pharmaceutically acceptable carrier.

9. The pharmaceutical composition of claim 8, wherein the pharmaceutically acceptable carrier comprises a buffering agent, a surfactant, a salt, an amino acid, an antioxidant, a sugar derivative, or a combination thereof.

10. The pharmaceutical composition of claim 9, wherein the sugar derivative is a non-reducing sugar, a sugar alcohol, a polyol, a disaccharide, or a polysaccharide.

11. A nucleic acid or a nucleic acid set, which collectively encode the isolated antibody set forth in claim 1.

12. The nucleic acid or nucleic acid set of claim 11, wherein the nucleic acid or nucleic acid set is a vector or a vector set.

13. The nucleic acid or nucleic acid set of claim 12, wherein the vector or the vector set is an expression vector or an expression vector set.

14. A host cell, comprising the vector or vector set of claim 12.

15. The host cell of claim 14, which is selected from the group consisting of a bacterial cell, a yeast cell, an insect cell, a plant cell, and a mammalian cell.

16. A method for producing an antibody binding to human GM-CSF, the method comprising:
   (i) culturing the host cell of claim 14 under conditions allowing for expressing of the antibody that binds human GM-CSF; and
   (ii) harvesting the cultured host cell or culture medium for collection of the antibody that binds human GM-CSF.

17. The method of claim 16, further comprising purifying the antibody that binds human GM-CSF.

18. The isolated antibody of claim 1, wherein the antibody comprises:
   (a) a $V_H$ comprising HC CDR1 of SEQ ID NO: 5, HC CDR2 of SEQ ID NO: 6, and HC CDR3 of SEQ ID NO: 31; and a $V_L$ comprising LC CDR1 of SEQ ID NO: 32, LC CDR2 of SEQ ID NO: 9, and LC CDR3 of SEQ ID NO: 10;
   (b) a $V_H$ comprising HC CDR1 of SEQ ID NO: 5, HC CDR2 of SEQ ID NO: 6, and HC CDR3 of SEQ ID NO: 33; and a $V_L$ comprising LC CDR1 of SEQ ID NO: 8, LC CDR2 of SEQ ID NO: 9, and LC CDR3 of SEQ ID NO: 10;
   (c) a $V_H$ comprising HC CDR1 of SEQ ID NO: HC CDR2 of SEQ ID NO: 6, and HC CDR3 of SEQ ID NO: 7; and a $V_L$ comprising LC CDR1 of SEQ ID NO: 32, LC CDR2 of SEQ ID NO: 9, and LC CDR3 of SEQ ID NO: 10;
   (d) a $V_H$ comprising HC CDR1 of SEQ ID NO: 5HC CDR2 of SEQ ID NO: 34, and HC CDR3 of SEQ ID NO: 7; and a $V_L$ comprising LC CDR1 of SEQ ID NO: 8, LC CDR2 of SEQ ID NO: 9, and LC CDR3 of SEQ ID NO: 10;
   (e) a $V_H$ comprising HC CDR1 of SEQ ID NO: 5; HC CDR2 of SEQ ID NO: 6, and HC CDR3 of SEQ ID NO: 7; and a $V_L$ comprising LC CDR1 of SEQ ID NO: 8, LC CDR2 of SEQ ID NO: 9, and LC CDR3 of SEQ ID NO: 35;
   (f) a $V_H$ comprising HC CDR1 of SEQ ID NO: 5, HC CDR2 of SEQ ID NO: 6, and HC CDR3 of SEQ ID NO: 36; and a $V_L$ comprising LC CDR1 of SEQ ID NO: 8, LC CDR2 of SEQ ID NO: 9, and LC CDR3 of SEQ ID NO: 10;
   (g) a $V_H$ comprising HC CDR1 of SEQ ID NO: 5, HC CDR2 of SEQ ID NO: 6, and HC CDR3 of SEQ ID NO: 37; and a $V_L$ comprising LC CDR1 of SEQ ID NO: 8, LC CDR2 of SEQ ID NO: 9, and LC CDR3 of SEQ ID NO: 10;
   (h) a $V_H$ comprising HC CDR1 of SEQ ID NO: 5, HC CDR2 of SEQ ID NO: 34, and HC CDR3 of SEQ ID NO: 7; and a $V_L$ comprising LC CDR1 of SEQ ID NO: 32, LC CDR2 of SEQ ID NO: 9, and LC CDR3 of SEQ ID NO: 10; or
   (i) a $V_H$ comprising HC CDR1 of SEQ ID NO: 5, HC CDR2 of SEQ ID NO: 6, and HC CDR3 of SEQ ID NO: 33; and a $V_L$ comprising LC CDR1 of SEQ ID NO: 32, LC CDR2 of SEQ ID NO: 9, and LC CDR3 of SEQ ID NO: 10.

* * * * *

SEQUENCE LISTING

```
<160> NUMBER OF SEQ ID NOS: 37

<210> SEQ ID NO 1
<211> LENGTH: 121
<212> TYPE: PRT
<213> ORGANISM: Artificial Sequence
<220> FEATURE:
<223> OTHER INFORMATION: Heavy chain variable domain sequence of 1D2

<400> SEQUENCE: 1

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Asp Lys
            20                  25                  30
```

```
Tyr Leu His Trp Val Arg Gln Ala Pro Gly Gln Gly Leu Glu Trp Met
            35                  40                  45

Ala Trp Ile Asn Pro Lys Ser Gly Gly Thr Phe Tyr Ala Gln Asn Phe
 50                  55                  60

Lys Gly Arg Val Thr Val Thr Arg Asp Thr Ser Ile Asn Thr Ala Tyr
 65                  70                  75                  80

Leu Glu Leu Thr Ser Leu Arg Leu Asp Asp Thr Ser Thr Tyr Tyr Cys
            85                  90                  95

Ala Arg Gly Arg Asp Tyr Tyr Asp Gln Gly Ala Ala Asp Leu Trp Gly
                100                 105                 110

Gln Gly Thr Met Val Thr Val Ser Ser
            115                 120

<210> SEQ ID NO 2
<211> LENGTH: 108
<212> TYPE: PRT
<213> ORGANISM: Artificial Sequence
<220> FEATURE:
<223> OTHER INFORMATION: Light chain variable domain sequence of 1D2

<400> SEQUENCE: 2

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Asn Ser Val
                20                  25                  30

Leu Ala Trp Tyr Gln Gln Lys Pro Gly Lys Ala Pro Lys Leu Leu Leu
            35                  40                  45

Tyr Ala Ala Ser Lys Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Gly Thr Tyr Tyr Cys Gln Gln Tyr Tyr Ser Pro Val Arg
            85                  90                  95

Thr Phe Gly Gln Gly Thr Lys Val Glu Ile Lys Arg
                100                 105

<210> SEQ ID NO 3
<211> LENGTH: 121
<212> TYPE: PRT
<213> ORGANISM: Artificial Sequence
<220> FEATURE:
<223> OTHER INFORMATION: Heavy chain variable domain sequences with D89E
      (ED) mutation

<400> SEQUENCE: 3

Gln Val Gln Leu Val Gln Ser Gly Ala Glu Val Lys Lys Pro Gly Ala
 1               5                  10                  15

Ser Val Lys Val Ser Cys Glu Ala Ser Gly Tyr Thr Phe Thr Asp Lys
                20                  25                  30

Tyr Leu His Trp Val Arg Gln Ala Pro Gly Gln Gly Leu Glu Trp Met
            35                  40                  45

Ala Trp Ile Asn Pro Lys Ser Gly Gly Thr Phe Tyr Ala Gln Asn Phe
 50                  55                  60

Lys Gly Arg Val Thr Val Thr Arg Asp Thr Ser Ile Asn Thr Ala Tyr
 65                  70                  75                  80

Leu Glu Leu Thr Ser Leu Arg Leu Glu Asp Thr Ser Thr Tyr Tyr Cys
            85                  90                  95
```

Ala Arg Gly Arg Asp Tyr Tyr Asp Gln Gly Ala Ala Asp Leu Trp Gly
            100                 105                 110

Gln Gly Thr Met Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Heavy chain variable domain sequences with D90E
      (DE) mutation

<400> SEQUENCE: 4

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Asp Lys
            20                  25                  30

Tyr Leu His Trp Val Arg Gln Ala Pro Gly Gln Gly Leu Glu Trp Met
        35                  40                  45

Ala Trp Ile Asn Pro Lys Ser Gly Gly Thr Phe Tyr Ala Gln Asn Phe
    50                  55                  60

Lys Gly Arg Val Thr Val Thr Arg Asp Thr Ser Ile Asn Thr Ala Tyr
65                  70                  75                  80

Leu Glu Leu Thr Ser Leu Arg Leu Asp Glu Thr Ser Thr Tyr Tyr Cys
                85                  90                  95

Ala Arg Gly Arg Asp Tyr Tyr Asp Gln Gly Ala Ala Asp Leu Trp Gly
            100                 105                 110

Gln Gly Thr Met Val Thr Val Ser Ser
        115                 120

<210> SEQ ID NO 5
<211> LENGTH: 8
<212> TYPE: PRT
<213> ORGANISM: Artificial Sequence
<220> FEATURE:
<223> OTHER INFORMATION: Heavy chain CDR1 of 1D2

<400> SEQUENCE: 5

Gly Tyr Thr Phe Thr Asp Lys Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Heavy chain CDR2 of 1D2

<400> SEQUENCE: 6

Ile Asn Pro Lys Ser Gly Gly Thr
1               5

<210> SEQ ID NO 7
<211> LENGTH: 14
<212> TYPE: PRT
<213> ORGANISM: Artificial Sequence
<220> FEATURE:
<223> OTHER INFORMATION: Heavy chain CDR3 of 1D2

<400> SEQUENCE: 7

Ala Arg Gly Arg Asp Tyr Tyr Asp Gln Gly Ala Ala Asp Leu
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Light chain CDR1 of 1D2

<400> SEQUENCE: 8

Gln Gly Ile Asn Ser Val
1               5

<210> SEQ ID NO 9

<400> SEQUENCE: 9

000

<210> SEQ ID NO 10
<211> LENGTH: 9
<212> TYPE: PRT
<213> ORGANISM: Artificial Sequence
<220> FEATURE:
<223> OTHER INFORMATION: Light chain CDR3 of 1D2

<400> SEQUENCE: 10

Gln Gln Tyr Tyr Ser Pro Val Arg Thr
1               5

<210> SEQ ID NO 11
<211> LENGTH: 8
<212> TYPE: PRT
<213> ORGANISM: Artificial Sequence
<220> FEATURE:
<223> OTHER INFORMATION: Variations in HC CDR1
<220> FEATURE:
<221> NAME/KEY: MUTAGEN
<222> LOCATION: (6)..(6)
<223> OTHER INFORMATION: Xaa can be D, E, S, P, G, A, V, N, Q, C, W, R,
      T, or L
<220> FEATURE:
<221> NAME/KEY: MUTAGEN
<222> LOCATION: (7)..(7)
<223> OTHER INFORMATION: Xaa can be K, V, L, E, P, S, T, C, D, R, H, A,
      F, Q, or N

<400> SEQUENCE: 11

Gly Tyr Thr Phe Thr Xaa Xaa Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Variations in in HC CDR2
<220> FEATURE:
<221> NAME/KEY: MUTAGEN
<222> LOCATION: (4)..(4)
<223> OTHER INFORMATION: Xaa can be K, L, M, E, H, S, V, N, C, F, P, W,
      G, A, I, R, T or Q

<400> SEQUENCE: 12

Ile Asn Pro Xaa Ser Gly Gly Thr
1               5

<210> SEQ ID NO 13
<211> LENGTH: 14
<212> TYPE: PRT

```
<213> ORGANISM: Artificial Sequence
<220> FEATURE:
<223> OTHER INFORMATION: Variations in HC CDR3
<220> FEATURE:
<221> NAME/KEY: MUTAGEN
<222> LOCATION: (4)..(4)
<223> OTHER INFORMATION: Xaa can be R, V, S, A, C, L, P, I, T, G, M, E,
      or Q
<220> FEATURE:
<221> NAME/KEY: MUTAGEN
<222> LOCATION: (6)..(6)
<223> OTHER INFORMATION: Xaa can be: Y, I, L, W, F, T, V, A, G, N, Y, or
      S
<220> FEATURE:
<221> NAME/KEY: MUTAGEN
<222> LOCATION: (7)..(7)
<223> OTHER INFORMATION: Xaa can be Y, N, P, S, K, R, G, W, D, Q, L, H,
      F, A, T, V, or M
<220> FEATURE:
<221> NAME/KEY: MUTAGEN
<222> LOCATION: (9)..(9)
<223> OTHER INFORMATION: Xaa can be Q, S, T, M, N, G, V, L, E, or W

<400> SEQUENCE: 13

Ala Arg Gly Xaa Asp Xaa Xaa Asp Xaa Gly Ala Ala Asp Leu
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Variations in LC CDR1
<220> FEATURE:
<221> NAME/KEY: MUTAGEN
<222> LOCATION: (6)..(6)
<223> OTHER INFORMATION: Xaa can be V, L, G, E, R, F, P, H, or Y

<400> SEQUENCE: 14

Gln Gly Ile Asn Ser Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Variations in LC CDR 3
<220> FEATURE:
<221> NAME/KEY: MUTAGEN
<222> LOCATION: (6)..(6)
<223> OTHER INFORMATION: Xaa can be P, R, N, or C
<220> FEATURE:
<221> NAME/KEY: MUTAGEN
<222> LOCATION: (7)..(7)
<223> OTHER INFORMATION: Xaa can be V, C, D. L, E, P, or R

<400> SEQUENCE: 15

Gln Gln Tyr Tyr Ser Xaa Xaa Arg Thr
1               5

<210> SEQ ID NO 16
<211> LENGTH: 5
<212> TYPE: PRT
<213> ORGANISM: Artificial Sequence
<220> FEATURE:
<223> OTHER INFORMATION: Heavy chain CDR1 of 1D2 in Kabat system

<400> SEQUENCE: 16

Asp Lys Tyr Leu His
1               5
```

<210> SEQ ID NO 17
<211> LENGTH: 17
<212> TYPE: PRT
<213> ORGANISM: Artificial Sequence
<220> FEATURE:
<223> OTHER INFORMATION: Heavy chain CDR2 of 1D2 in Kabat system

<400> SEQUENCE: 17

Trp Ile Asn Pro Lys Ser Gly Gly Thr Phe Tyr Ala Gln Asn Phe Lys
1               5                   10                  15
Gly

<210> SEQ ID NO 18
<211> LENGTH: 12
<212> TYPE: PRT
<213> ORGANISM: Artificial Sequence
<220> FEATURE:
<223> OTHER INFORMATION: Heavy chain CDR3 of 1D2 in Kabat system

<400> SEQUENCE: 18

Gly Arg Asp Tyr Tyr Asp Gln Gly Ala Ala Asp Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Light chain CDR1 of 1D2 in Kabat system

<400> SEQUENCE: 19

Arg Ala Ser Gln Gly Ile Asn Ser Val Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Light chain CDR2 of 1D2 in Kabat system

<400> SEQUENCE: 20

Ala Ala Ser Lys Leu Glu Ser
1               5

<210> SEQ ID NO 21
<211> LENGTH: 8
<212> TYPE: PRT
<213> ORGANISM: Artificial Sequence
<220> FEATURE:
<223> OTHER INFORMATION: Variations in HC CDR1
<220> FEATURE:
<221> NAME/KEY: MUTAGEN
<222> LOCATION: (6)..(6)
<223> OTHER INFORMATION: Xaa can be E, S, P, G, A, V, N, Q, C, W, R, T,
      or L

<400> SEQUENCE: 21

Gly Tyr Thr Phe Thr Xaa Lys Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Variations in HC CDR1

```
<220> FEATURE:
<221> NAME/KEY: MUTAGEN
<222> LOCATION: (7)..(7)
<223> OTHER INFORMATION: Xaa can be V, L, E, P, S, T, C, D, R, H, A, F,
      Q, or N

<400> SEQUENCE: 22

Gly Tyr Thr Phe Thr Asp Xaa Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Variations in HC CDR2
<220> FEATURE:
<221> NAME/KEY: MUTAGEN
<222> LOCATION: (4)..(4)
<223> OTHER INFORMATION: Xaa can be K, M, E, H, S, V, N, C, F, P, W, G,
      A, I, R, T or Q

<400> SEQUENCE: 23

Ile Asn Pro Xaa Ser Gly Gly Thr
1               5

<210> SEQ ID NO 24
<211> LENGTH: 14
<212> TYPE: PRT
<213> ORGANISM: Artificial Sequence
<220> FEATURE:
<223> OTHER INFORMATION: Variations in HC CDR3
<220> FEATURE:
<221> NAME/KEY: MUTAGEN
<222> LOCATION: (4)..(4)
<223> OTHER INFORMATION: Xaa can be V, S, A, C, L, P, I, T, G, M, E, or
      Q

<400> SEQUENCE: 24

Ala Arg Gly Xaa Asp Tyr Tyr Asp Gln Gly Ala Ala Asp Leu
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Variations in HC CDR3
<220> FEATURE:
<221> NAME/KEY: MUTAGEN
<222> LOCATION: (6)..(6)
<223> OTHER INFORMATION: Xaa can be I, L, W, F, T, V, A, G, N, Y, or S

<400> SEQUENCE: 25

Ala Arg Gly Arg Asp Xaa Tyr Asp Gln Gly Ala Ala Asp Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Variations in HC CDR3
<220> FEATURE:
<221> NAME/KEY: MUTAGEN
<222> LOCATION: (7)..(7)
<223> OTHER INFORMATION: Xaa can be N, P, S, K, R, G, W, D, Q, L, H, F,
      A, T, V, or M

<400> SEQUENCE: 26
```

Ala Arg Gly Arg Asp Tyr Xaa Asp Gln Gly Ala Ala Asp Leu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Variations in HC CDR3
<220> FEATURE:
<221> NAME/KEY: MUTAGEN
<222> LOCATION: (9)..(9)
<223> OTHER INFORMATION: Xaa can be S, T, M, N, G, V, L, E, or W

<400> SEQUENCE: 27

Ala Arg Gly Arg Asp Tyr Tyr Asp Xaa Gly Ala Ala Asp Leu
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Variations in LC CDR1
<220> FEATURE:
<221> NAME/KEY: MUTAGEN
<222> LOCATION: (6)..(6)
<223> OTHER INFORMATION: Xaa can be L, G, E, R, F, P, H, or Y

<400> SEQUENCE: 28

Gln Gly Ile Asn Ser Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Variations in LC CDR3
<220> FEATURE:
<221> NAME/KEY: MUTAGEN
<222> LOCATION: (6)..(6)
<223> OTHER INFORMATION: Xaa can be R, N or C

<400> SEQUENCE: 29

Gln Gln Tyr Tyr Ser Xaa Val Arg Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Variations in LC CDR3
<220> FEATURE:
<221> NAME/KEY: MUTAGEN
<222> LOCATION: (7)..(7)
<223> OTHER INFORMATION: Xaa can be C, D, L, E, P, or R

<400> SEQUENCE: 30

Gln Gln Tyr Tyr Ser Pro Xaa Arg Thr
1               5

<210> SEQ ID NO 31
<211> LENGTH: 14
<212> TYPE: PRT
<213> ORGANISM: Artificial Sequence
<220> FEATURE:
<223> OTHER INFORMATION: Heavy chain CDR3 of 103R in IMGT system

```
<400> SEQUENCE: 31

Ala Arg Gly Arg Asp Tyr Arg Asp Gln Gly Ala Ala Asp Leu
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Light chain CDR1 of 32R in IMGT system

<400> SEQUENCE: 32

Gln Gly Ile Asn Ser Arg
1               5

<210> SEQ ID NO 33
<211> LENGTH: 14
<212> TYPE: PRT
<213> ORGANISM: Artificial Sequence
<220> FEATURE:
<223> OTHER INFORMATION: Heavy chain CDR3 of 103N in IMGT system

<400> SEQUENCE: 33

Ala Arg Gly Arg Asp Tyr Asn Asp Gln Gly Ala Ala Asp Leu
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Heavy chain CDR2 of 54G in IMGT system

<400> SEQUENCE: 34

Ile Asn Pro Gly Ser Gly Gly Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Light chain CDR3 of 94N in IMGT system

<400> SEQUENCE: 35

Gln Gln Tyr Tyr Ser Asn Val Arg Thr
1               5

<210> SEQ ID NO 36
<211> LENGTH: 14
<212> TYPE: PRT
<213> ORGANISM: Artificial Sequence
<220> FEATURE:
<223> OTHER INFORMATION: Heavy chain CDR3 of 100G in IMGT system

<400> SEQUENCE: 36

Ala Arg Gly Gly Asp Tyr Tyr Asp Gln Gly Ala Ala Asp Leu
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Heavy chain CDR3 of 105N in IMGT system
```

```
<400> SEQUENCE: 37

Ala Arg Gly Arg Asp Tyr Tyr Asp Asn Gly Ala Ala Asp Leu
1               5                   10
```